US011213825B2

(12) United States Patent
Schwartz et al.

(10) Patent No.: US 11,213,825 B2
(45) Date of Patent: Jan. 4, 2022

(54) SYSTEM AND METHOD FOR EN MASSE PATTERNING OF MOLECULE STRUCTURES

(71) Applicants:Wisconsin Alumni Research Foundation, Madison, WI (US); University of Leiden, Leiden (NL); University of Chicago, Chicago, IL (US)

(72) Inventors: David Charles Schwartz, Madison, WI (US); Kristy L. Kounovsky-Shafer, Kearney, NE (US); Juan Pablo Hernandez-Ortiz, Madison, WI (US); Konstantinos Dimitrios Potamousis, Madison, WI (US); Juan Jose De Pablo, Chicago, IL (US); Theo Odijk, Leiden (NL); Kyubong Jo, Seoul (KR)

(73) Assignees: Wisconsin Alumni Research Foundation, Madison, WI (US); University of Leiden, Leiden (NL); University of Chicago, Chicago, IL (US)

( * ) Notice: Subject to any disclaimer, the term of this patent is extended or adjusted under 35 U.S.C. 154(b) by 182 days.

(21) Appl. No.: 16/614,003

(22) PCT Filed: May 16, 2018

(86) PCT No.: PCT/US2018/032987
§ 371 (c)(1),
(2) Date: Nov. 15, 2019

(87) PCT Pub. No.: WO2018/213459
PCT Pub. Date: Nov. 22, 2018

(65) Prior Publication Data
US 2020/0078789 A1    Mar. 12, 2020

Related U.S. Application Data

(60) Provisional application No. 62/506,992, filed on May 16, 2017.

(51) Int. Cl.
*B01L 3/00* (2006.01)
*G01N 27/447* (2006.01)
*G01N 33/487* (2006.01)

(52) U.S. Cl.
CPC .. *B01L 3/502761* (2013.01); *G01N 27/44791* (2013.01); *G01N 33/48721* (2013.01);
(Continued)

(58) Field of Classification Search
CPC ....... B01L 3/502761; B01L 2200/0663; B01L 2300/0645; B01L 2300/0896; G01N 27/44791; G01N 33/48721
See application file for complete search history.

(56) References Cited

U.S. PATENT DOCUMENTS

2015/0075984 A1  3/2015  Schwartz et al.
2015/0252141 A1  9/2015  Bai et al.

FOREIGN PATENT DOCUMENTS

WO    2016/036647 A1    3/2016

OTHER PUBLICATIONS

International Search Report and Written Opinion from parent PCT/US2018/032987, dated Aug. 17, 2018, 15 pages.

*Primary Examiner* — Jennifer Wecker
*Assistant Examiner* — Kathryn Elizabeth Limbaugh
(74) *Attorney, Agent, or Firm* — Quarles & Brady LLP

(57) ABSTRACT

Devices, systems, and methods for en masse patterning of nucleic acid molecule structures are disclosed. The devices can include microchannels and nanoslits. The microchannels and nanoslits can be connected by parking chambers. The systems and methods can utilize the geometry of the devices
(Continued)

in coordination with a voltage application routine to park nucleic acid molecules in the parking chambers and subsequently inject the nucleic acid molecules into the nanoslits. The methods can be utilized to present nucleic acid molecules in a fashion suitable for genomic analysis. The methods can also be utilized to provide size selection of the nucleic acid molecules.

19 Claims, 18 Drawing Sheets

(52) U.S. Cl.
CPC ............... *B01L 2200/0663* (2013.01); *B01L 2300/0645* (2013.01); *B01L 2300/0896* (2013.01)

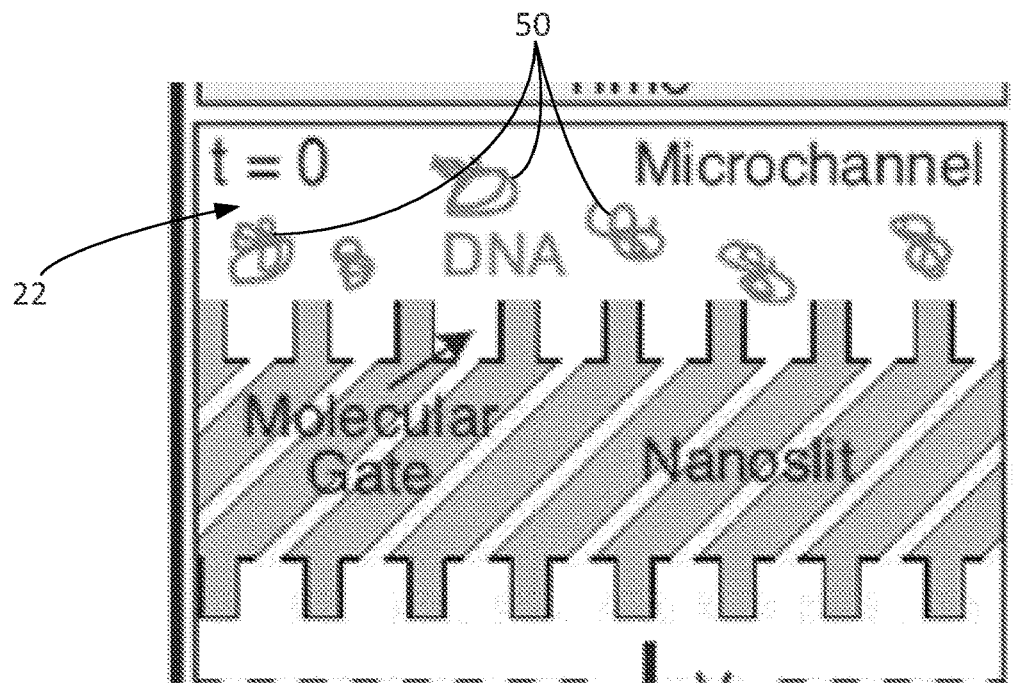
FIG. 3B1
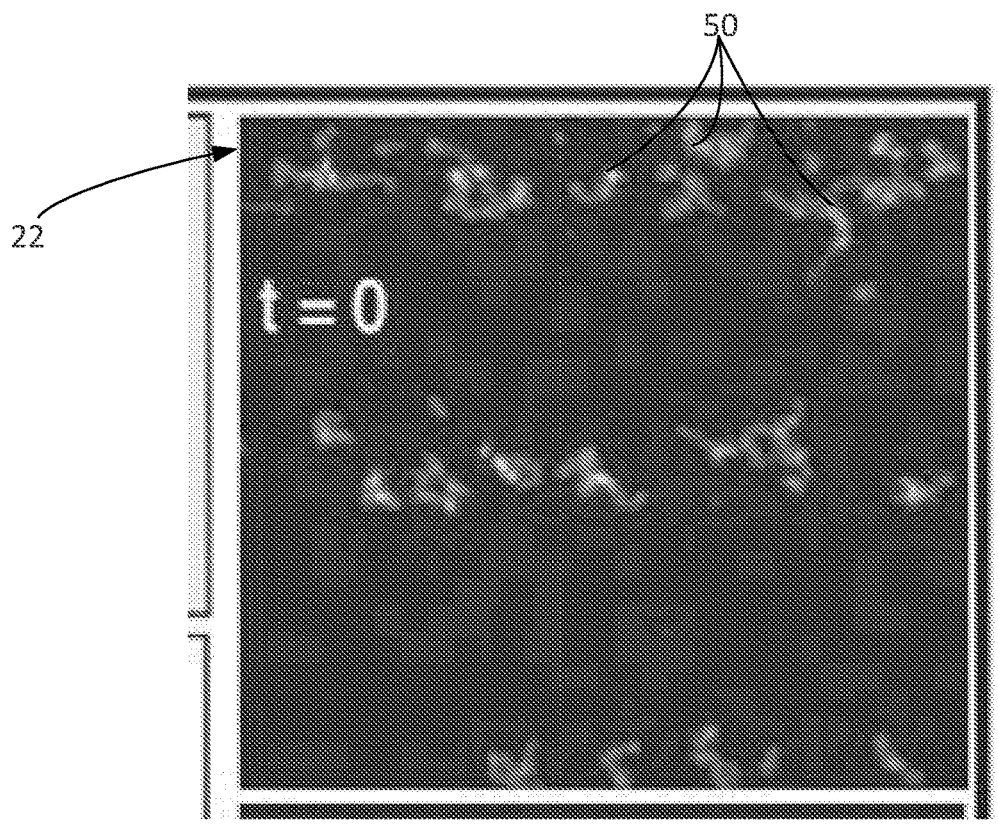
FIG. 3B2

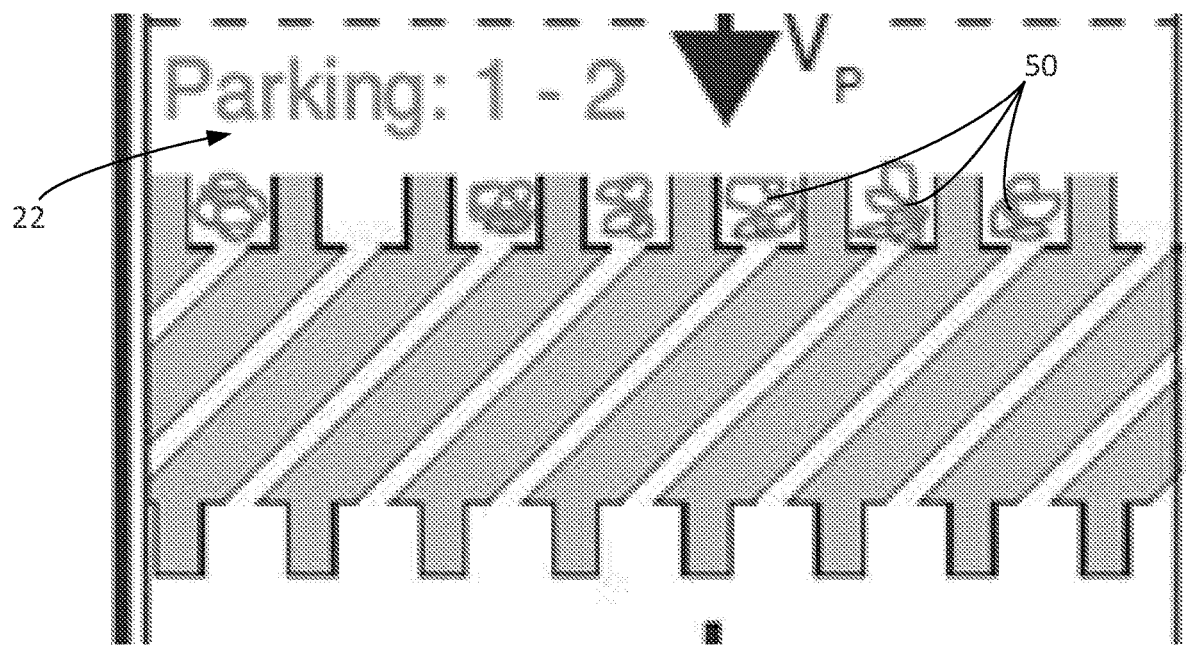
FIG. 3C1
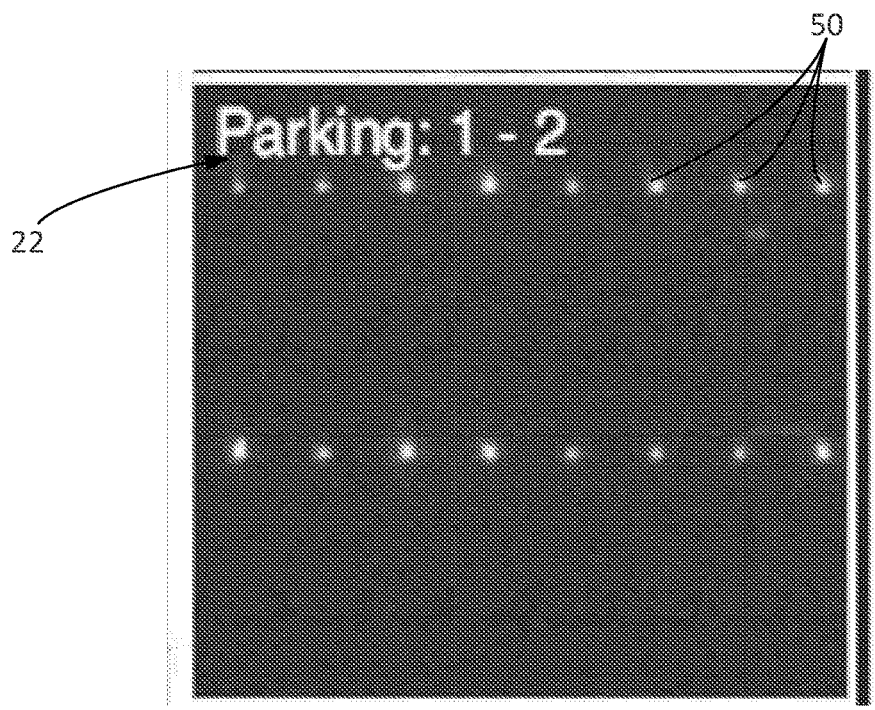
FIG. 3C2

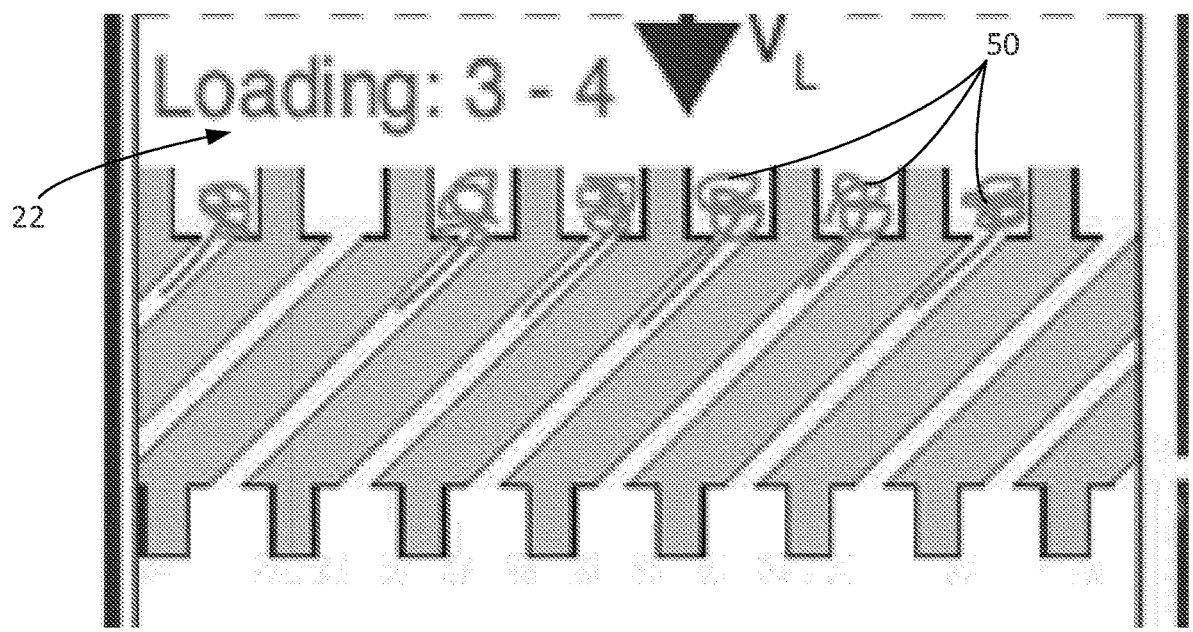
FIG. 3D1
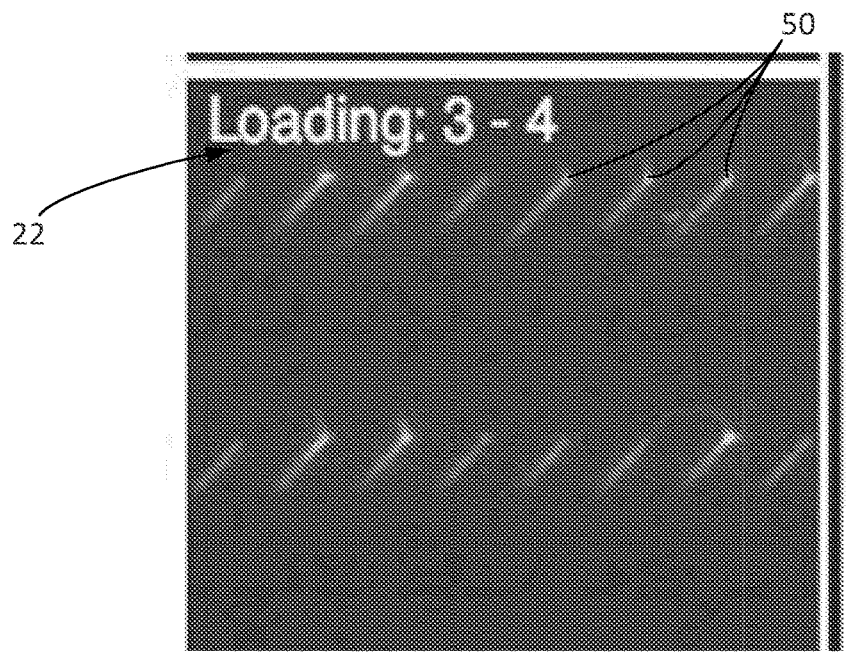
FIG. 3D2

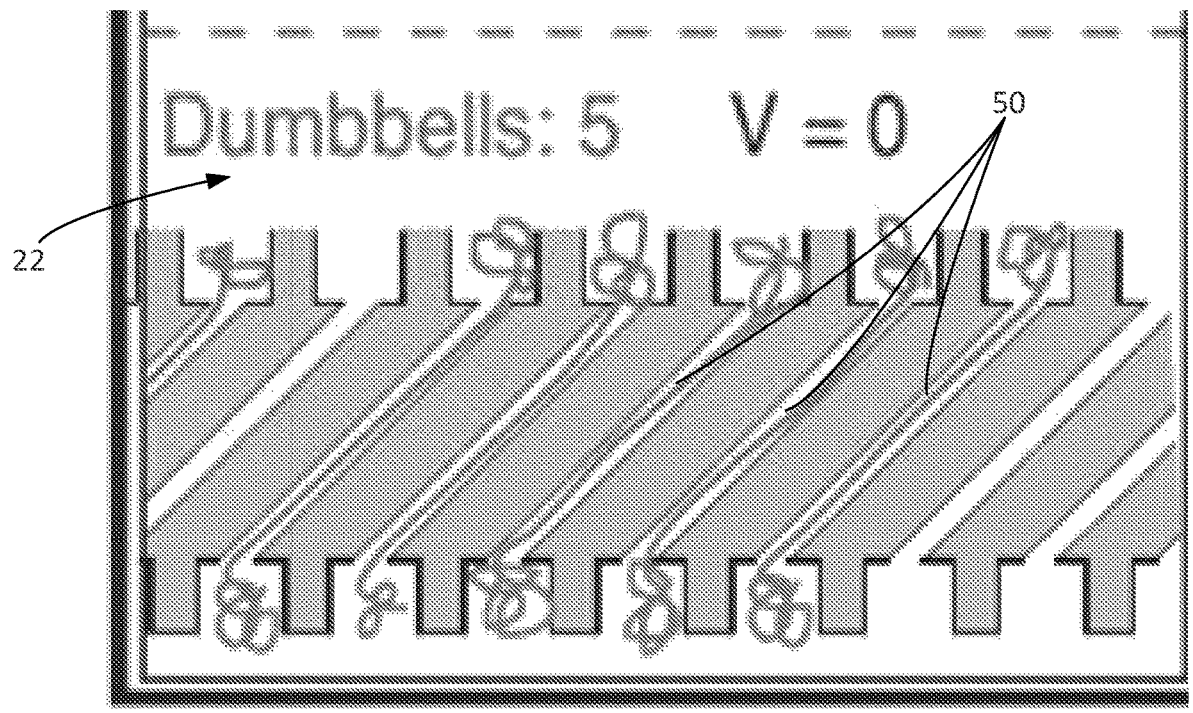
FIG. 3E1
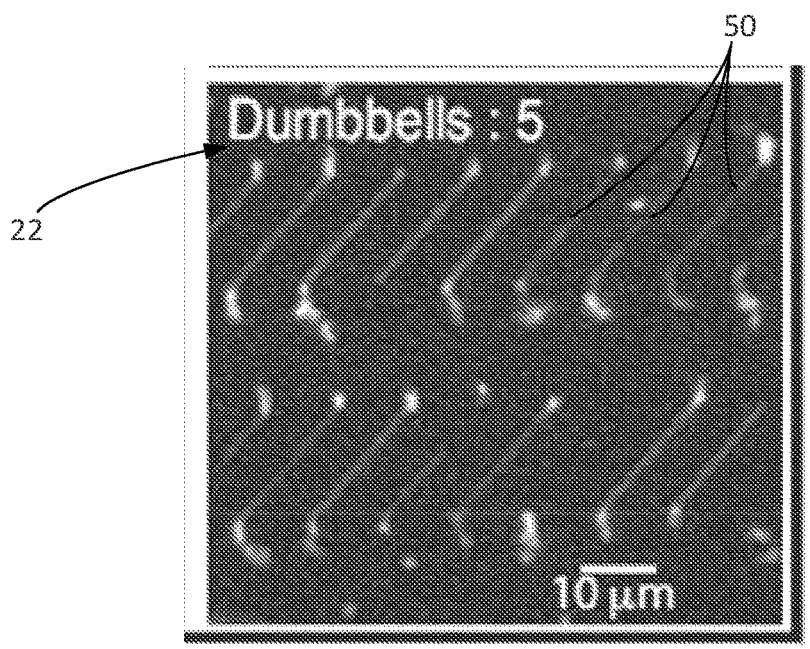
FIG. 3E2

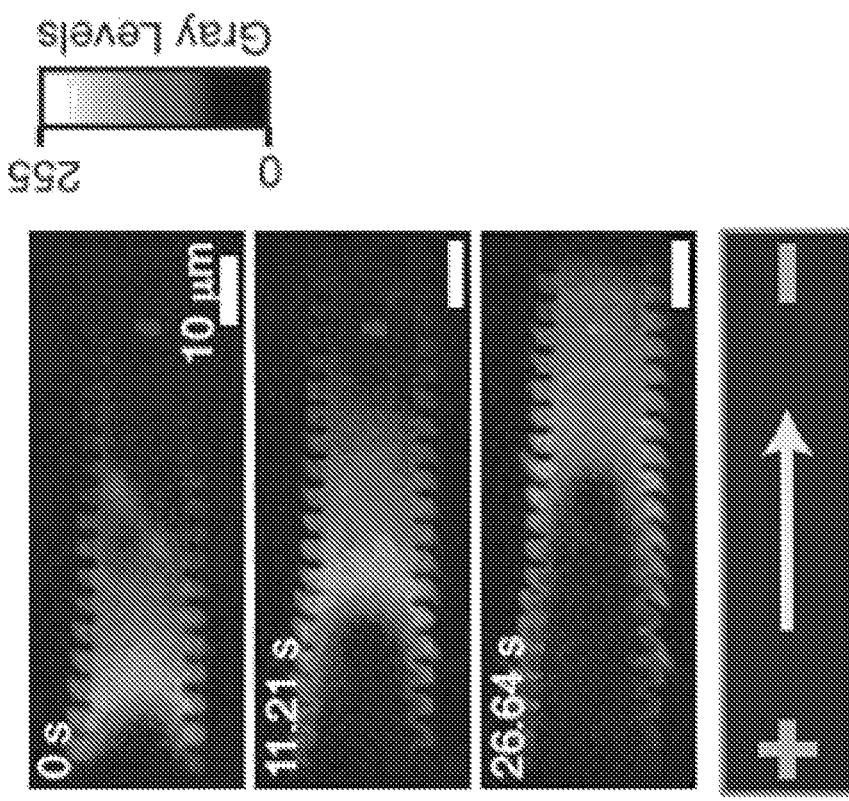
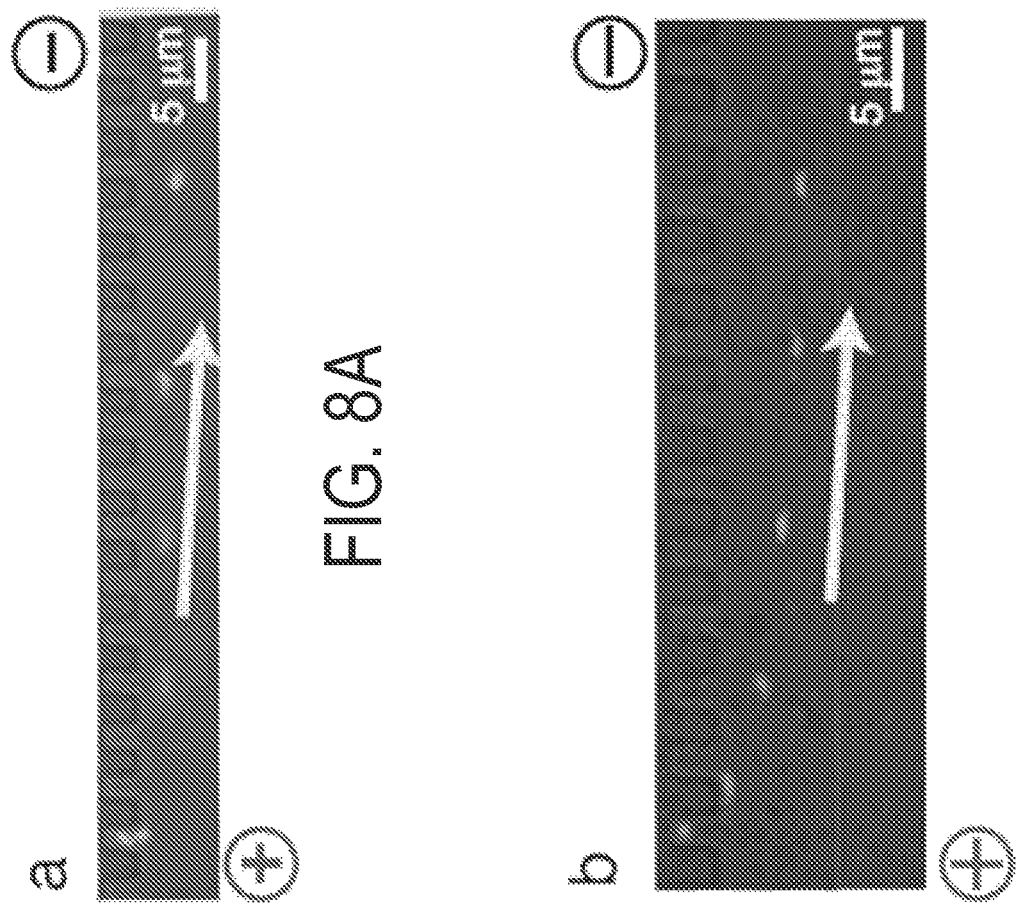
FIG. 8A  FIG. 8B  FIG. 8C

SYSTEM AND METHOD FOR EN MASSE PATTERNING OF MOLECULE STRUCTURES

CROSS-REFERENCE TO RELATED APPLICATIONS

This application is a 371 U.S. National Phase Patent Application of PCT/US2018/032987, filed May 16, 2018, which claims the benefit of U.S. Provisional Patent Application No. 62/506,992, filed May 16, 2017, each of which is incorporated by reference herein in its entirety for all purposes.

STATEMENT REGARDING FEDERALLY SPONSORED RESEARCH

This invention was made with government support under HG000225 awarded by the National Institutes of Health. The government has certain rights in the invention.

BACKGROUND OF THE INVENTION

The field of the invention is molecule manipulation. More particularly, the invention relates to stretching nucleic acid molecules in order to better present portions of the nucleic acid molecules for inspection by various techniques or to isolate various different populations of nucleic acid molecules.

The Precision Medicine Initiative is pressing for the development of new approaches for knowing the molecular underpinnings of disease through the detailed measurement of individuals, which may ramp up to a large cohort of 1 million participants. Meeting this challenge means that genome analysis approaches must advance to become more informative across the entire human genome, while at the same time offer dramatic reductions of cost. Accordingly, systems employing single molecule analytes have emerged, but not without much teething pain. Early single molecule sequencing systems have pointed the way forward to meeting these challenges, but despite costly commercialization efforts by Pacific Biosciences and Oxford Nanopore, issues still remain to be solved for moving industrialized versions of these systems into widespread use within biomedical settings.

Single molecule approaches to human genome mapping provide a counterpart to sequencing efforts through discernment of structural variation (SV), in ways that elude sequence analysis. The invention of Optical Mapping and its advanced version—Nanocoding, now being commercialized by BioNanoGenomics, are offering insights in to structural variation present in normal human and cancer genomes. Such variants are difficult to fully characterize by sequencing because the human genome comprises vast stretches of complex, repeat-ridden regions harboring SVs that were comprehensively functionalized by the ENCODE Project. The new insights provided by ENCODE are substantiating the biological importance of these previously neglected portions within the human genome and this new knowledge is also motivating development of new technologies that readily reveal complex variants.

As such, previous work from one or more of the present inventors dealt with these issues through development of a robust DNA labeling and presentation approach, "Nanocoding," which barcodes molecules with nicking restriction enzymes whose cleavage sites are then marked by nick translation using fluorochrome-labeled nucleotides. Thusly formed punctates are imaged by Fluorescence Resonance Energy Transfer (FRET) microscopy along stretched molecules using nanoconfinement regimes leveraging low ionic strength (I) conditions. Because the DNA persistence length increases with lowered solution ionic strength, these conditions synergized DNA stretching within relatively large slits. Other groups, later, built upon these developments. More specifically, the first nanoslit devices developed in these efforts were fabricated from PDMS using soft lithography techniques that featured high aspect ratio slits (100 nm×1, 000 nm). Although much smaller slit dimensions are required for stretching DNA molecules, confinement conditions were greatly enhanced by using electrostatic effects mediated by very low ionic strength conditions (~0.2 mM). Later work modified slit geometries (250 nm×400 nm) and ionic strength conditions, which further enhanced DNA stretch ($\hat{S}=S/L=0.88$, where L is the molecule contour length), but loading molecules into the nanoslits became more difficult. This is a common problem affecting most nanofluidic devices since the entropic cost is substantial when threading large random coil molecules into slit geometries comparable to the DNA persistence length.

Early investigations revealed that large DNA molecules, under low ionic strength conditions, would sometimes partially load into nanoslits (100 nm×1,000 nm), but were bracketed outside of the slits by random coil portions that formed "DNA dumbbells". Importantly, DNA molecules in a dumbbell conformation showed enhanced stretching (S=S/L=1.06), which cannot be the result of the vanishingly small entropic forces exerted by the "molecular lobes." Instead, theoretical treatments and simulations identified the combined effects of electrostatic and hydrodynamic interactions (HI) as the dominant factors mediating enhanced stretching.

A need remains to further understand and then harness electrostatic effects and DNA polymer dynamics within nanofluidic systems in ways that would readily load and present very large DNA molecules as dumbbells. These are important considerations since DNA dumbbells, when formed by random loading events, would be difficult to produce en masse.

Accordingly, a need exists for an approach to synchronized formation of nucleic acid molecule dumbbells that overcomes the aforementioned drawbacks.

SUMMARY OF THE INVENTION

The present invention overcomes the aforementioned drawbacks by providing systems and methods for en masse patterning of nucleic acid molecules.

The present disclosure provides the devices, systems, and methods that are described, stated, and claimed herein.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 2A1 is an image showing loading of loading chambers under low ionic strength conditions, in accordance with an aspect of the present disclosure.

FIG. 2A2 is an image showing attempted loading of loading chambers under high ionic strength conditions, in accordance with an aspect of the present disclosure.

FIG. 3B1 is an illustration of a portion of the system of FIG. 1B, shown prior to the application of the power supply routine, in accordance with an aspect of the present disclosure.

FIG. 3B2 is an image of the configuration shown in FIG. 3B1, in accordance with an aspect of the present disclosure.

FIG. 3C1 is an illustration of the portion of the system of FIG. 3B1, shown in a molecule or particle of interest parking configuration, in accordance with an aspect of the present disclosure.

FIG. 3C2 is an image of the configuration shown in FIG. 3C1, in accordance with an aspect of the present disclosure.

FIG. 3D1 is an illustration of the portion of the system of FIG. 3B1, shown in a molecule or particle of interest loading configuration, in accordance with an aspect of the present disclosure.

FIG. 3D2 is an image of the configuration shown in FIG. 3D1.

FIG. 3E1 is an illustration of the portion of the system of FIG. 3B1, shown in a molecule or particle of interest dumbbell configuration, in accordance with an aspect of the present disclosure.

FIG. 3E2 is an image of the configuration shown in FIG. 3E1.

FIG. 8A is a superimposed image showing loading dynamics of fluorescent labeled carboxyl terminated polystyrene microspheres, in accordance with an aspect of the present disclosure.

FIG. 8B is a superimposed image showing loading dynamics of fluorescent labeled native polystyrene microspheres, in accordance with an aspect of the present disclosure.

FIG. 8C is a series of images showing migration of neutral Rhodamine B dye, in accordance with an aspect of the present disclosure.

DETAILED DESCRIPTION OF THE INVENTION

All referenced patents, applications, and non-patent literature cited in this disclosure are incorporated herein by reference in their entirety. If a reference and this disclosure disagree, then this disclosure is controlling.

The present disclosure provides devices, systems, and methods as described in the statements below, the claims, and the present description.

Whenever a molecule, molecule of interest, nucleic acid molecule, or nucleic acid molecule of interest is referenced herein, the present disclosure also contemplates deformable objects, such as particles, with or without an effective charge, random coil proteins, synthetic polyelectrolytes, chromatin, synthetic polymers, and the like. For uncharged objects, diaphoretic forces could provide the transport described herein with respect to charged objects or molecules and the corresponding forces.

Figure 1A:
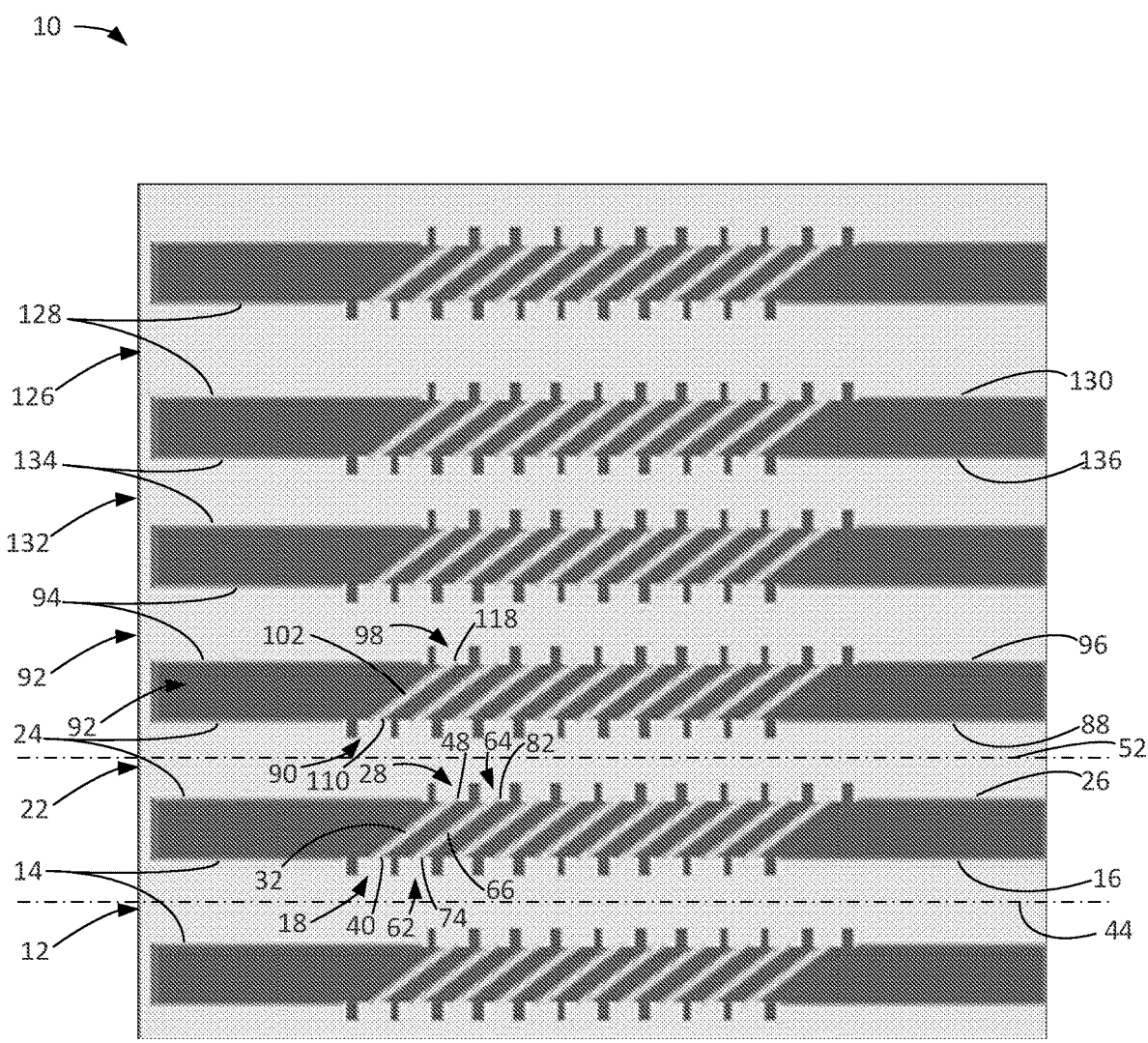
FIG. 1A is a top view of a schematic of a device, in accordance with an aspect of the present disclosure.

Referring to FIG. 1A, a microfluidic device 10 is shown in accordance with aspects of the present disclosure. The microfluidic device 10 comprises a primary microchannel 12 defined by primary microchannel walls 14 having a primary distal microchannel surface 16 with a first primary distal microchannel opening 18, the primary microchannel 12 having a primary microchannel height (distance into the page as shown in FIG. 1A). The microfluidic device 10 further comprises a secondary microchannel 22 defined by secondary microchannel walls 24 having a secondary proximal microchannel surface 26 with a first secondary proximal microchannel opening 28, the secondary microchannel 22 having a secondary microchannel height (distance into the page as shown in FIG. 1A). As used herein, walls can refer to surfaces bounding a space or volume in any direction (in other words, walls includes "ceilings" and "floors" of a space or volume, so a closed cubic space could be described as having six walls).

The microfluidic device 10 further comprises a first primary nanoslit 32 having a first primary nanoslit height (into the page as shown in FIG. 1A), a first primary nanoslit width (similar to the second primary nanoslit width 36, shown in FIG. 1E), and a first primary nanoslit length (i.e., the length of the first primary nanoslit 32 from the primary distal microchannel surface 16 to the secondary proximal microchannel surface 26).

The microfluidic device 10 further comprises a first primary proximal parking chamber 40 having a first primary proximal parking chamber height (distance into the page as shown in FIG. 1A), a first primary proximal parking chamber width (axial distance along a lengthwise axis 44 of the primary microchannel 12), and a first primary proximal parking chamber length (radial distance, with respect to the lengthwise axis 44). The first primary nanoslit 32 is connected to the first primary proximal parking chamber 40. The first primary proximal parking chamber 40 is connected to the primary microchannel 12 via the first primary distal microchannel opening 18. The first primary nanoslit 32 is in fluid communication with the secondary microchannel 22 via the first secondary proximal microchannel opening 28.

In some non-limiting examples, the first primary proximal parking chamber 40 is configured to be occupied by an integer number of molecules or particles of interest 50 (shown in FIGS. 3A-3E2), each having a coiled structure, and to exclude additional molecules or particles of interest 50 from entry. In some instances, the integer number of molecules or particles of interest 50 is a single molecule or particle of interest. In some instances, the integer number of molecules or particles of interest 50 and/or the additional molecules or particles of interest 50 are nucleic acid molecules.

The microfluidic device 10 further comprises a first primary distal parking chamber 48 having a first primary distal parking chamber height (distance into the page as shown in FIG. 1A), a first primary distal parking chamber width (axial distance along a lengthwise axis 52 of the secondary microchannel 22), and a first primary distal parking chamber length (radial distance, with respect to the lengthwise axis 52). The first primary nanoslit 32 is connected to the first primary distal parking chamber 48. The first primary distal parking chamber 48 is connected to the secondary microchannel 22 via the first secondary proximal microchannel opening 28.

In some instances, the first primary proximal parking chamber 40 has a first primary proximal parking chamber volume of between 1 nm³ and 1 mm³. In some other instances, the first primary proximal parking chamber volume is between 1 µm³ and 250 µm³. In yet some other instances, the first primary distal parking chamber 48 has a first primary distal parking chamber volume of between 1 nm³ and 1 mm³. In still some other instances, the first primary distal parking chamber volume is between 1 µm³ and 250 µm³.

In some non-limiting examples, the first primary proximal parking chamber height is between 1% and 125% of the primary microchannel height. In some instances, the first primary proximal parking chamber height is between 75% and 100% of the primary microchannel height. In some instances, the first primary distal parking chamber height is between 1% and 125% of the secondary microchannel height. In some instances, the first primary distal parking chamber height is between 75% and 100% of the secondary microchannel height. In some instances, the first primary proximal parking chamber height is between 10 nm and 10 mm, between 100 nm and 50 µm, or between 1.0 µm and 5.0 µm. In some instances, the first primary proximal parking chamber width is between 10 nm and 10 mm, between 100 nm and 50 µm, or between 1.0 µm and 5.0 µm. In some instances, the first primary proximal parking chamber length is between 10 nm and 10 mm, between 100 nm and 50 µm, or between 1.0 µm and 10.0 µm. In some instances, the first primary distal parking chamber height is between 10 nm and 10 mm, between 100 nm and 50 µm, or between 1.0 µm and 5.0 µm. In some instances, the first primary distal parking chamber width is between 10 nm and 10 mm, between 100 nm and 50 µm, or between 1.0 µm and 5.0 µm. In some instances, the first primary distal parking chamber length is between 10 nm and 10 mm, between 100 nm and 50 µm, or between 1.0 µm and 10.0 µm. In some instances, the first primary nanoslit height 34 is less than 50%, less than 25%, or less than 10% of the first primary proximal parking chamber height. In some instances, the first primary nanoslit height 34 is less than or equal to 100 nm. In some instances, the first primary nanoslit width is less than 50%, less than 25%, or less than 10% of the first primary proximal parking chamber width. In some instances, the first primary nanoslit width is less than or equal to 1 µm. In some instances, the first primary nanoslit length is between 1 µm and 10 mm. In some instances, the first primary nanoslit length is between 10 µm and 100 µm.

In some instances, the first primary nanoslit 32 is oriented at an angle of between 1° and 89° relative to the lengthwise axis 44 of the primary microchannel 12. In some instances, the first primary nanoslit 32 is oriented at an angle of between 10° and 80° relative to the lengthwise axis 44 of the primary microchannel 12. In some instances, the first primary nanoslit 32 is oriented at an angle of between 40° and 50° relative to the lengthwise axis 44 of the primary microchannel 12.

In some instances, the first primary nanoslit 32 has a first primary nanoslit cross-sectional area that is less than 25% of a first primary proximal parking chamber cross-sectional area of the first primary proximal parking chamber 40. In some instances, the primary distal microchannel surface 16 and the secondary proximal microchannel surface 26 are separated by a primary microchannel separation 60 distance of between 1 µm and 10 mm. In some instances, the primary microchannel separation 60 distance is between 5 µm and 1 mm or between 10 µm and 100 µm.

As illustrated, the primary distal microchannel surface 16 further comprises a second primary distal microchannel opening 62. The secondary proximal microchannel surface 26 has a second secondary proximal microchannel opening 64.

The microfluidic device 10 further comprises a second primary nanoslit 66 having a second primary nanoslit height (into the page as shown in FIG. 1A), the second primary nanoslit width 36 (shown in FIG. 1E), and a second primary nanoslit length (i.e., the length of the second primary nanoslit 66 from the primary distal microchannel surface 16 to the secondary proximal microchannel surface 26).

The microfluidic device 10 further comprises a second primary proximal parking chamber 74 having a second primary proximal parking chamber height (into the page as shown in FIG. 1A), a second primary proximal parking chamber width (axial distance along a lengthwise axis 44 of the primary microchannel 12), and a second primary proximal parking chamber length (radial distance, with respect to the lengthwise axis 44). The second primary nanoslit 66 is connected to the second primary proximal parking chamber 74. The second primary proximal parking chamber 74 is connected to the primary microchannel 12 via the second primary distal microchannel opening 62. The second primary nanoslit 66 is in fluid communication with the secondary microchannel 22 via the second secondary proximal microchannel opening 64.

In some instances, the microfluidic device 10 further comprises a second primary distal parking chamber 82 having a second primary distal parking chamber height (into the page as shown in FIG. 1A), a second primary distal parking chamber width (axial distance along a lengthwise axis 52 of the secondary microchannel 22), and a second primary distal parking chamber length (radial distance, with respect to the lengthwise axis 52). The second primary nanoslit 66 is connected to the second primary distal parking chamber 82. The second primary distal parking chamber 82 is connected to the secondary microchannel 22 via the second secondary proximal microchannel opening 64.

In some instances, the primary distal microchannel surface 16 further includes a plurality of primary distal microchannel openings, substantially similar to the first and second primary distal microchannel openings 18, 62. The secondary proximal microchannel surface 26 further includes a plurality of secondary proximal microchannel openings, substantially similar to the first and second secondary proximal microchannel openings 28, 64.

In some non-limiting examples, the microfluidic device 10 further comprises a plurality of primary nanoslits, substantially similar to the first and second primary nanoslits 32, 66. The microfluidic device 10 further comprises a plurality of primary proximal parking chambers, substantially similar to the first and second primary proximal parking chambers 40, 74. Each of the plurality of primary proximal nanoslits is connected to a respective one of the plurality of primary proximal parking chambers. Each of the plurality of primary proximal parking chambers is connected to the primary microchannel 12 via a respective one of the plurality of primary distal microchannel openings. Each of the plurality of primary nanoslits is in fluid communication with the secondary microchannel 22 via a respective one of the plurality of secondary proximal microchannel openings.

In some instances, the microfluidic device 10 further comprises a plurality of primary distal parking chambers, substantially similar to the first and second primary distal parking chambers 48, 82. Each of the plurality of primary nanoslits is connected to a respective one of the plurality of primary distal parking chambers. Each of the plurality of primary distal parking chambers is connected to the second microchannel 22 via a respective one of the plurality of secondary proximal microchannel openings.

In some instances, the second primary proximal parking chamber 74, the second primary distal parking chamber 82, one or more of the plurality of primary proximal parking chambers, or one or more of the plurality of primary distal parking chambers has a parking chamber volume of between 1 nm$^3$ and 1 mm$^3$ or between 1 μm$^3$ and 250 μm$^3$.

In some instances, each of the plurality of primary proximal parking chambers or each of the plurality of primary distal parking chambers is configured to be occupied by an integer number of the molecules or particles of interest 50 or a single molecule or particle of interest 50 in a coiled structure and to exclude additional molecules or particles of interest 50 from entry.

In some instances, the plurality of primary proximal parking chambers each has a primary proximal parking chamber height of between 1% and 125% or between 75% and 100% of the primary microchannel height.

In some instances, the plurality of primary distal parking chambers each has a primary distal parking chamber height of between 1% and 125% or between 75% and 100% of the secondary microchannel height.

In some instances, the plurality of primary proximal parking chambers each has a primary proximal parking chamber height of between 10 nm and 10 mm, between 100 nm and 50 μm, or between 1.0 μm and 5.0 μm.

In some instances, each of the plurality of primary proximal parking chambers has a primary proximal parking chamber width of between 10 nm and 10 mm, between 100 nm and 50 μm, or between 1.0 μm and 5.0 μm.

In some instances, each of the plurality of primary proximal parking chambers has a primary proximal parking chamber length of between 10 nm and 10 mm, between 100 nm and 50 μm, or between 1.0 μm and 10.0 μm.

In some instances, each of the plurality of primary distal parking chambers has a primary distal parking chamber height of between 10 nm and 10 mm, between 100 nm and 50 μm, or 1.0 μm and 5.0 μm.

In some instances, each of the plurality of primary distal parking chambers has a primary distal parking chamber width of between 10 nm and 10 mm, between 100 nm and 50 μm, or 1.0 μm and 5.0 μm.

In some instances, each of the plurality of primary distal parking chambers has a primary distal parking chamber length of between 10 nm and 10 mm, between 100 nm and 50 μm, or 1.0 μm and 10.0 μm.

In some instances, each of the plurality of primary nanoslits has a primary nanoslit height of less than 50%, less than 25%, or less than 10% of a corresponding primary proximal parking chamber height for the respective one of the plurality of primary proximal parking chambers to which each of the plurality of primary nanoslits is connected.

In some instances, the primary nanoslit height is less than or equal to 100 nm.

In some instances, each of the plurality of primary nanoslits has a primary nanoslit width of less than 50%, less than 25%, or less than 10% of a corresponding primary proximal parking chamber width for the respective one of the plurality of primary proximal parking chambers to which each of the plurality of primary nanoslits is connected.

In some instances, the primary nanoslit width is less than or equal to 1 μm.

In some instances, each of the plurality of primary nanoslits has a primary nanoslit length of between 1 μm and 10 mm or between 10 μm and 100 μm.

In some instances, each of the plurality of primary nanoslits is oriented at an angle of between 1° and 89°, between 10° and 80°, or between 40° and 50° relative to the lengthwise axis 44 of the primary microchannel 12.

In some instances, each of the plurality of primary nanoslits has a primary nanoslit cross-sectional area that is less than 25% of a primary proximal parking chamber cross-sectional area of the respective one of the plurality of primary proximal parking chambers to which each of the plurality of primary nanoslits is connected.

In some instances, the plurality of primary nanoslits are substantially parallel with one another. In some instances, the plurality of primary nanoslits are substantially the same length. In some instances, the plurality of primary nanoslits have a statistical distribution of different lengths. In some instances, the plurality of primary nanoslits include at least 100 primary nanoslits. In some instances, the plurality of primary nanoslits include at least 500 nanoslits. In some instances, the plurality of primary nanoslits include at least 1000 nanoslits.

Figure 1B:
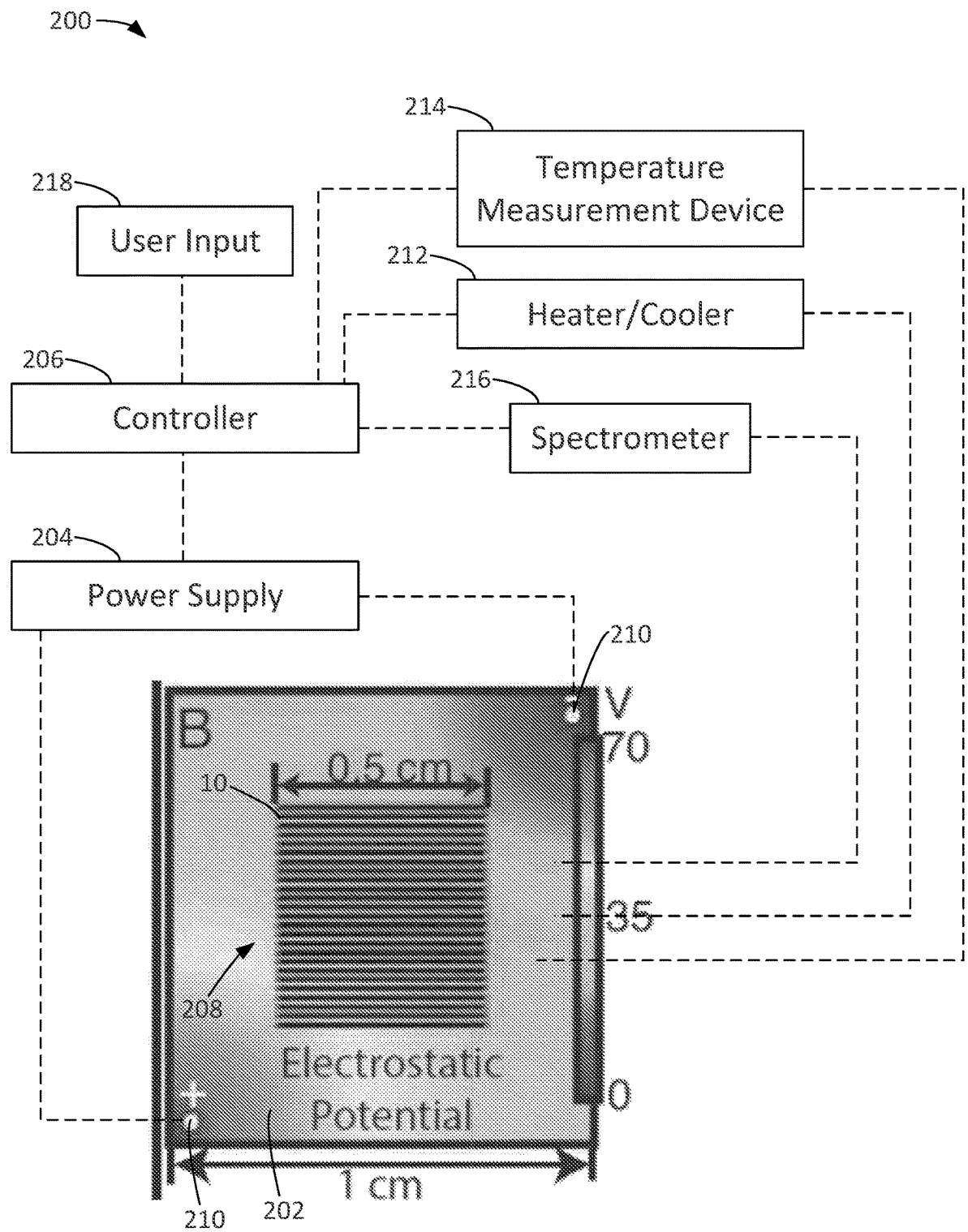
FIG. 1B is a plot of electrostatic potential across a device within a system, in accordance with an aspect of the present disclosure.
Figure 1C:
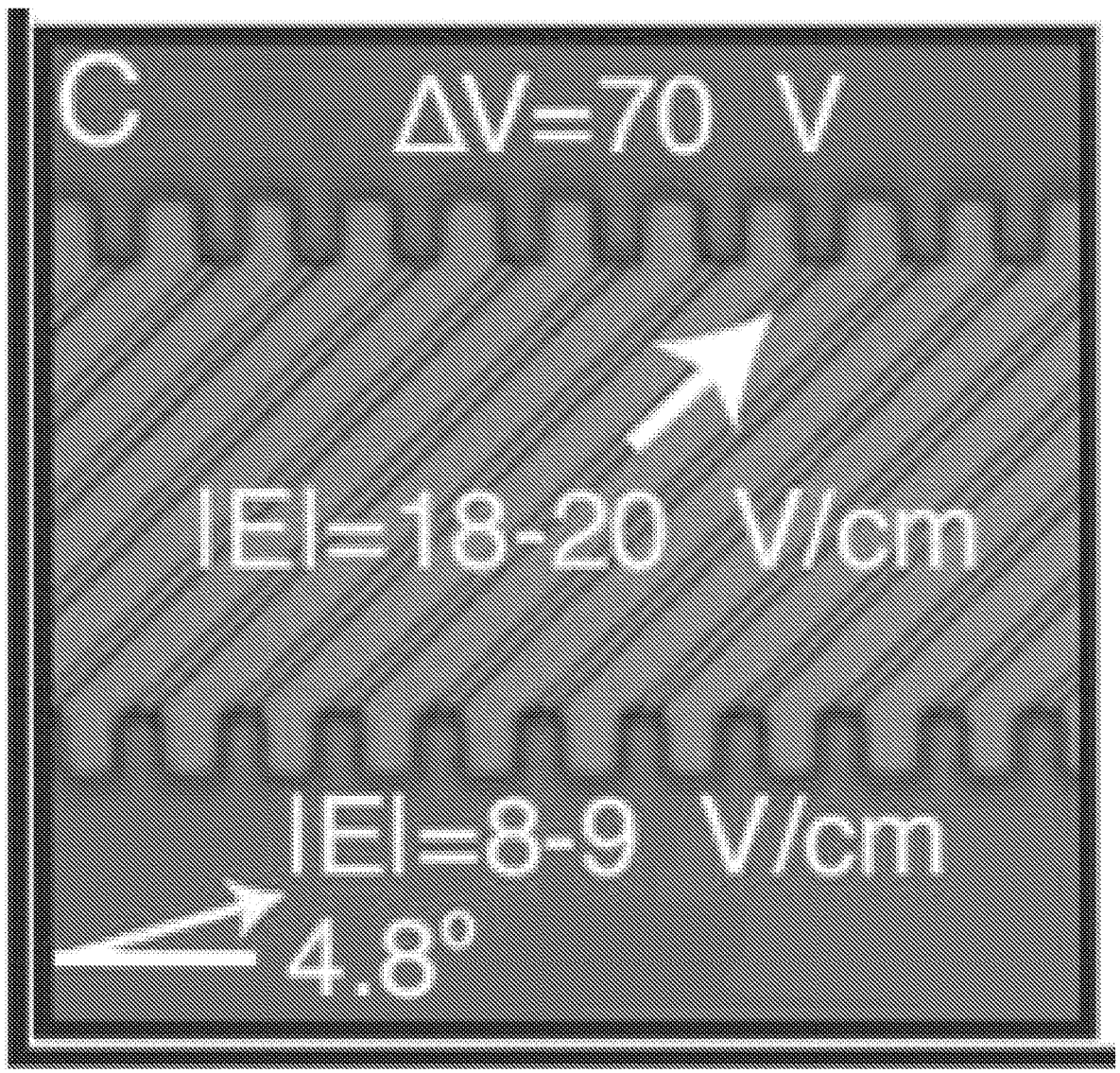
FIG. 1C is a microscopy image of a device, in accordance with an aspect of the present disclosure.
Figure 1D:
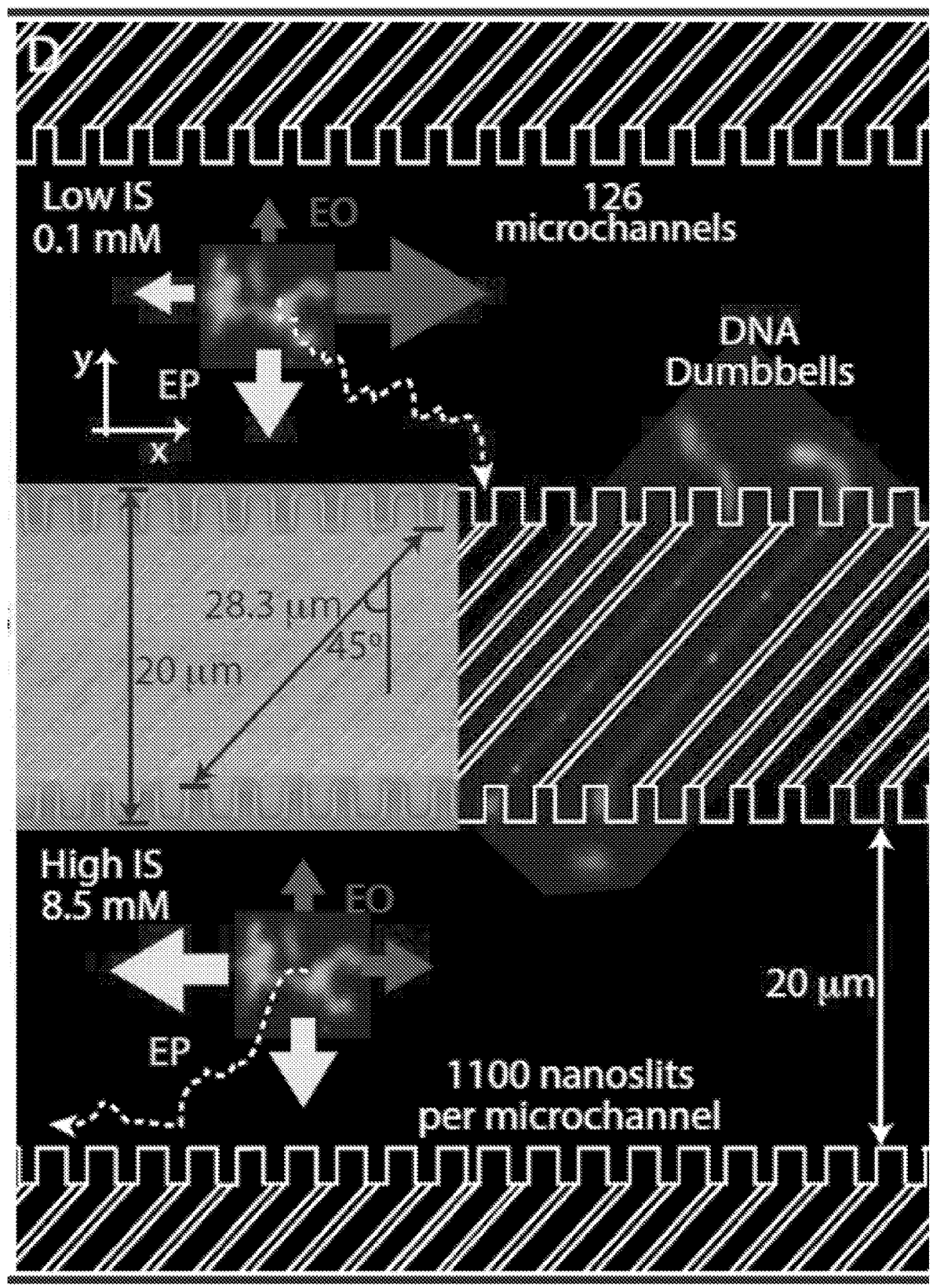
FIG. 1D is a mixed schematic and microscopy image of a device showing various forces acting on molecules of interest, in accordance with the present disclosure.
Figure 1E:
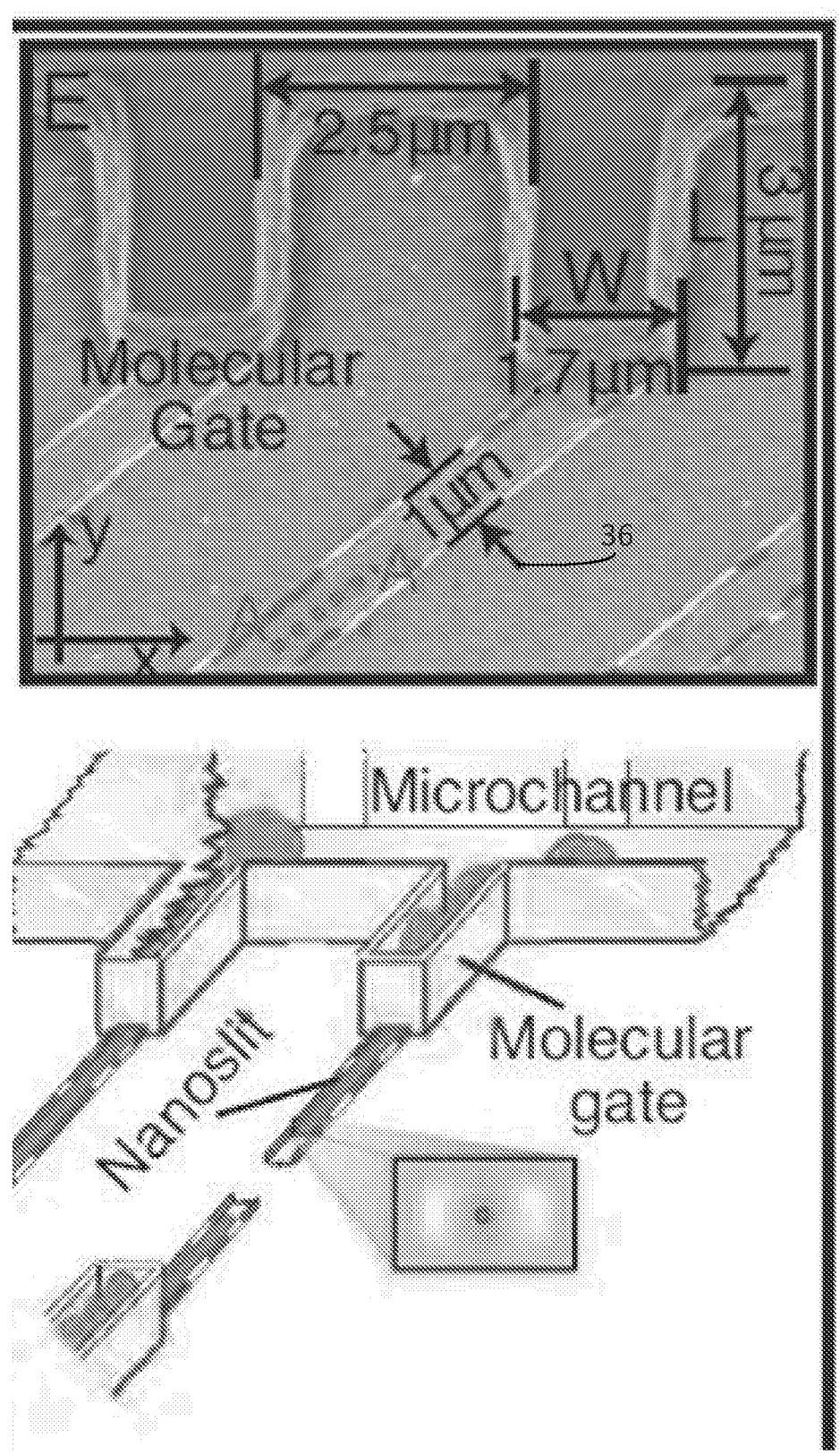
FIG. 1E is a scanning electron microscope image of loading chambers (top) and an illustration of a device showing illustrating ion distributions of loaded nanoslits, in accordance with an aspect of the present disclosure.
Figure 1F:
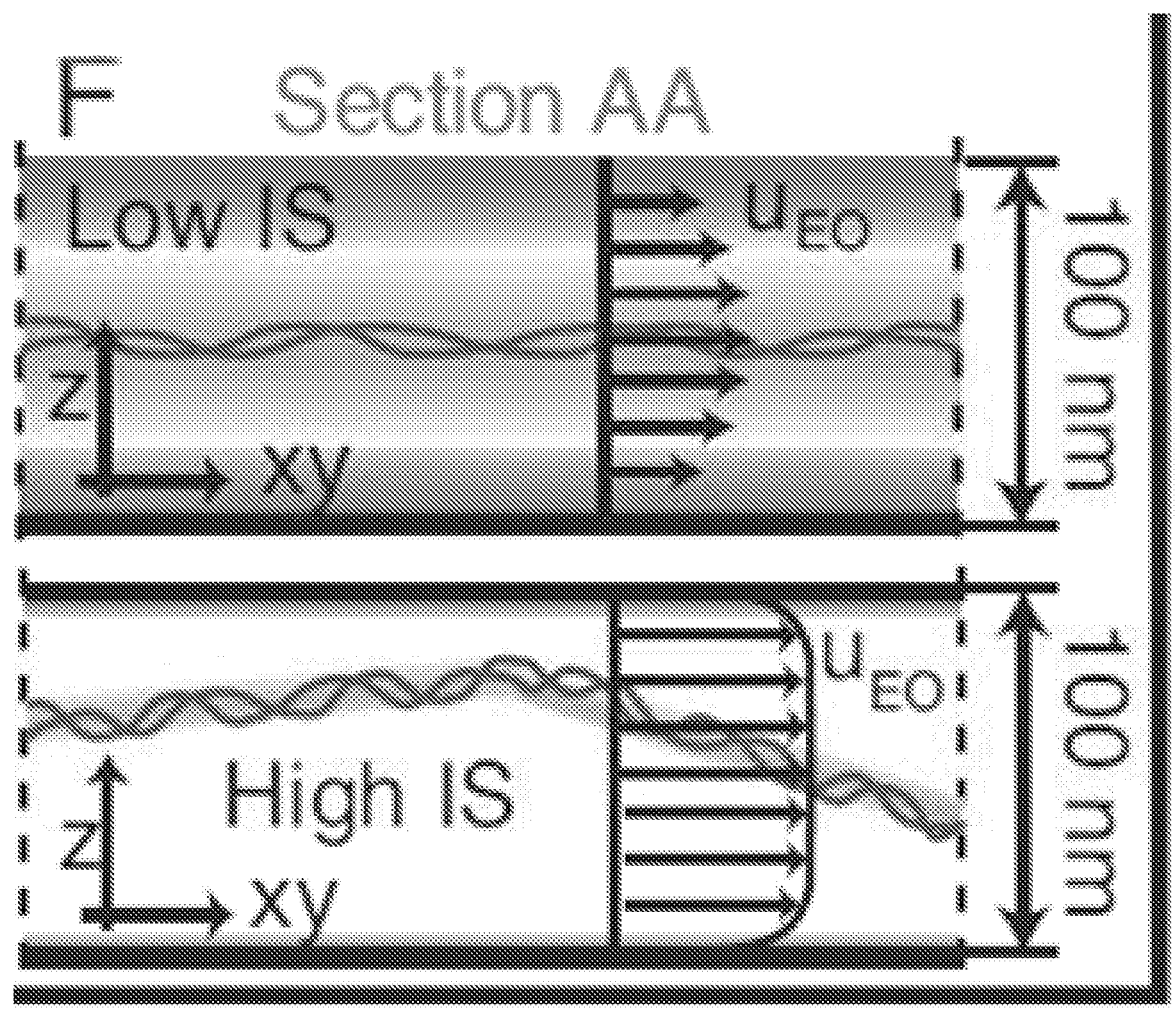
FIG. 1F is a perspective drawing of a nanoslit showing ion clouds under low and high ionic strength conditions, in accordance with an aspect of the present disclosure.

In some instances, the plurality of primary distal parking chambers are separated by a primary distal parking chamber separation distance 86 (shown in FIG. 1E). The primary distal parking chamber separation distance 86 may be between 1 nm and 1 mm, between 100 nm and 100 μm, or between 1 μm and 25 μm. The plurality of primary proximal parking chambers are separated by a primary parking chamber separation distance, substantially similar to the primary distal parking chamber separation distance 86, of between 1 nm and 1 mm, between 100 nm and 100 μm, or between 1 μm and 25 μm.

In some non-limiting examples, the secondary microchannel walls 24 have a secondary distal microchannel surface 88 with a first secondary distal microchannel opening 90. The microfluidic device 10 further comprises a tertiary microchannel 92 defined by tertiary microchannel walls 94 having a tertiary proximal microchannel surface 96 with a first tertiary proximal microchannel opening 98. The tertiary microchannel 92 has a tertiary microchannel height (into the page as shown in FIG. 1A).

The microfluidic device 10 further comprises a first secondary nanoslit 102 having a first secondary nanoslit height (into the page as shown in FIG. 1A), a first secondary nanoslit width (similar to the second primary nanoslit width 36), and a first secondary nanoslit length (i.e., the length of the first secondary nanoslit 102 from the secondary distal microchannel surface 88 to the tertiary proximal microchannel surface 96).

The microfluidic device 10 further comprises a first secondary proximal parking chamber 110 having a first secondary proximal parking chamber height (into the page as shown in FIG. 1A), a first secondary proximal parking chamber width (similar to each of the other parking chamber widths), and a first secondary proximal parking chamber length (similar to each of the other parking chamber lengths). The first secondary nanoslit 102 is connected to the first secondary proximal parking chamber 110. The first secondary proximal parking chamber 110 is connected to the secondary microchannel 22 via the first secondary distal microchannel opening 90. The first secondary nanoslit 102 is in fluid communication with the tertiary microchannel 92 via the first tertiary proximal microchannel opening 98.

In some instances, the microfluidic device 10 further comprises a first secondary distal parking chamber 118 having a first secondary distal parking chamber height (similar to each of the other parking chamber heights), a first secondary distal parking chamber width (similar to each of the other parking chamber widths), and a first secondary distal parking chamber length (similar to each of the other parking chamber lengths). The first secondary nanoslit 102 is connected to the first secondary distal parking chamber 118. The first secondary distal parking chamber 118 is connected to the tertiary microchannel 92 via the first tertiary proximal microchannel opening 98.

In some instances, the secondary distal microchannel surface 88 further includes a plurality of secondary distal microchannel openings, substantially similar to the secondary distal microchannel opening 90. The tertiary proximal microchannel surface 96 has a plurality of tertiary proximal microchannel openings, substantially similar to the first tertiary proximal microchannel opening 98. The microfluidic device 10 further comprises a plurality of secondary nanoslits, substantially similar to the first secondary nanoslit 102. The microfluidic device 10 further comprises a plurality of secondary proximal parking chambers, substantially similar to the first secondary proximal parking chamber 110. Each of the plurality of secondary proximal nanoslits is connected to a respective one of the plurality of secondary proximal parking chambers. Each of the plurality of secondary proximal parking chambers is connected to the secondary microchannel 22 via a respective one of the plurality of secondary distal microchannel openings, each of the plurality of primary nanoslits is in fluid communication with the tertiary microchannel 92 via a respective one of the plurality of tertiary proximal microchannel openings.

In some instances, the microfluidic device 10 further comprises a plurality of secondary distal parking chambers, which can be substantially similar to the first secondary distal parking chamber 118. Each of the plurality of secondary nanoslits is connected to a respective one of the plurality of secondary distal parking chambers. Each of the plurality of secondary distal parking chambers is connected to the tertiary microchannel 92 via a respective one of the plurality of tertiary proximal microchannel openings.

In some instances, the microfluidic device 10 further comprises a plurality of microchannels, substantially similar to the primary, secondary, and tertiary microchannels 12, 22, 92. Each of the plurality of microchannels is defined by microchannel walls having a distal microchannel surface with a plurality of distal microchannel openings. The microchannel walls each have a proximal microchannel surface with a plurality of proximal microchannel openings.

The microfluidic device 10 further comprises a series of pluralities of nanoslits and a series of pluralities of proximal parking chambers. Each of the nanoslits in the series of pluralities of nanoslits is connected to a respective proximal parking chamber of the series of pluralities of proximal parking chambers. Each of the proximal parking chambers in the series of pluralities of proximal parking chambers is connected to a respective proximal microchannel of the plurality of microchannels via a respective proximal microchannel opening of the plurality of proximal microchannel openings. Each of the nanoslits in the series of pluralities of nanoslits is in fluid communication with a respective distal microchannel via a respective distal microchannel opening of the plurality of distal microchannel openings. The respective distal microchannel neighbors the respective proximal microchannel.

In some non-limiting examples, the microfluidic device 10 further comprises a series of pluralities of distal parking chambers. Each of the nanoslits in the series of pluralities of nanoslits is connected to a respective distal parking chamber of the series of pluralities of distal parking chambers. Each of the distal parking chambers in the series of pluralities of distal parking chambers is connected to the respective distal microchannel of the plurality of microchannels.

In some instances, the plurality of microchannels are open-ended. In some instances, the plurality of microchannels are evenly spaced. In some instances, the plurality of microchannels are spaced by a statistical distribution of different distances.

In some non-limiting examples, the microfluidic device 10 further comprises a terminal microchannel 126 defined by terminal microchannel walls 128 having a terminal proximal microchannel surface 130 with a plurality of terminal proximal microchannel openings, substantially similar to the proximal microchannel openings 28, 64, 98. The primary microchannel 12 and the terminal microchannel 126 are positioned at opposite ends of the plurality of microchannels. The plurality of microchannels includes a penultimate microchannel 132 that is nearest to the terminal microchannel 126, the penultimate microchannel 132 defined by penultimate microchannel walls 134 having a penultimate distal microchannel surface 136 with a plurality of penultimate distal microchannel openings, substantially similar to the distal microchannel openings 18, 62, 90.

The microfluidic device 10 further comprises a plurality of terminal nanoslits, a plurality of terminal proximal parking chambers, and a plurality of terminal distal parking chambers, substantially similar to the nanoslits 32, 66, 102, the proximal parking chambers 40, 74, 110, and the distal parking chambers 48, 82, 118. Each of the plurality of terminal nanoslits is connected to a respective terminal proximal parking chamber of the plurality of terminal proximal parking chambers. Each of the plurality of terminal nanoslits is connected to a respective terminal distal parking chamber of the plurality of terminal distal parking chambers. Each of the plurality of terminal proximal parking chambers is connected to the penultimate microchannel 132 via a respective one of the plurality of penultimate distal microchannel openings. Each of the plurality of terminal distal parking chambers is connected to the terminal microchannel 126 via a respective one of the plurality of terminal proximal microchannel openings.

In some instances, the primary microchannel 12 and the terminal microchannel 126 are in fluid communication.

In some instances, at least 50%, at least 75%, or at least 90% of all nanoslits within the microfluidic device 10 are occupied by one and only one molecule or particle of interest or nucleic acid molecule of interest.

Referring to FIG. 1B, in some non-limiting examples, the microfluidic device 10 described above may be implemented in a system 200. The system 200 includes the microfluidic device 10, a device receiving chamber 202, a power supply 204, and a power supply controller 206.

The device receiving chamber 202 comprises a device orienting portion 208 and at least two electrodes 210, the device orienting portion 208 configured to receive the microfluidic device 10 and reproducibly orient the microfluidic device 10 relative to at least two electrodes 210. The power supply 204 is in electronic communication with the at least two electrodes 210. The power supply controller 206 is configured to execute a power supply routine.

The system 200 further comprises a heater or a cooler 212 configured to heat or cool liquid within the microfluidic device 10 and/or within the device receiving chamber 202.

The system 200 further comprises a temperature measurement device 214 configured to measure a temperature of fluid within the microfluidic device and/or the device receiving chamber 202.

The system 200 further comprises a spectrometer 216 configured to optically interrogate molecules located in the microfluidic device. The spectrometer 216 has sufficient spatial resolution to distinguish between molecules located in adjacent nanoslits. The spectrometer 216 is configured to monitor an occupancy status of one or more parking chambers and/or one or more nanoslits. The spectrometer 216 can be a fluorescence microscope. The system 200 may further comprise a user input 218, such as a computing device input known to those having ordinary skill in the art (e.g., keyboard and mouse, microphone and voice-recognition software, touchscreen, etc.).

In some instances the power supply controller 206 is programmed with or configured to receive nucleic acid electrostatic or hydrodynamic information regarding molecules or particles of interest 50, microfluidic device electrostatic or hydrodynamic information regarding the microfluidic device 10, buffer ionic strength information regarding a buffer of interest, or a combination thereof.

Figure 2B:
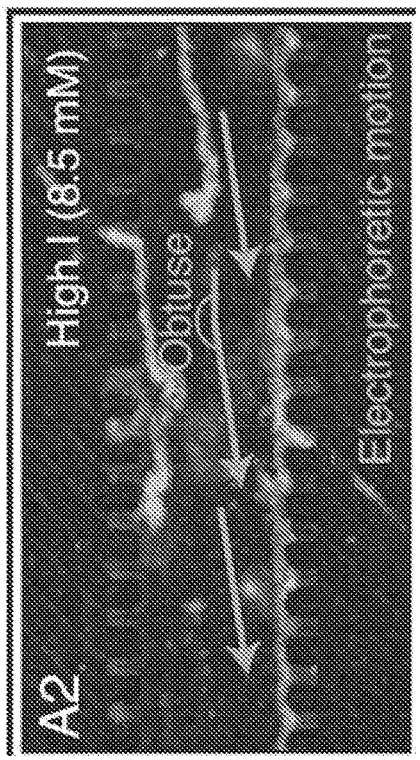
FIG. 2B is a plot of loading efficiency versus ionic strength, in accordance with an aspect of the present disclosure.
Figure 2B:
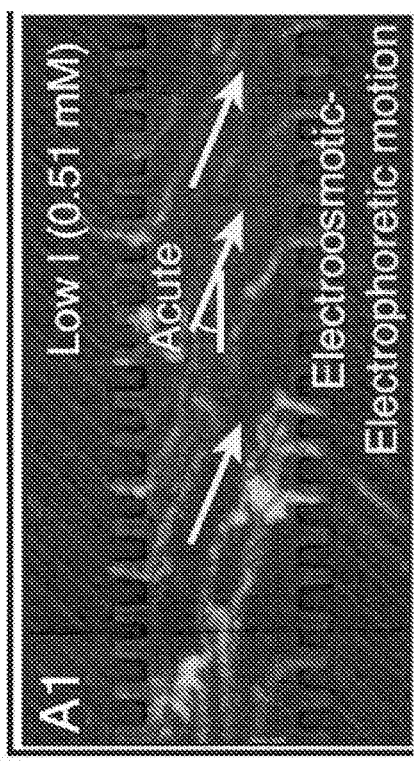
Figure 2B:
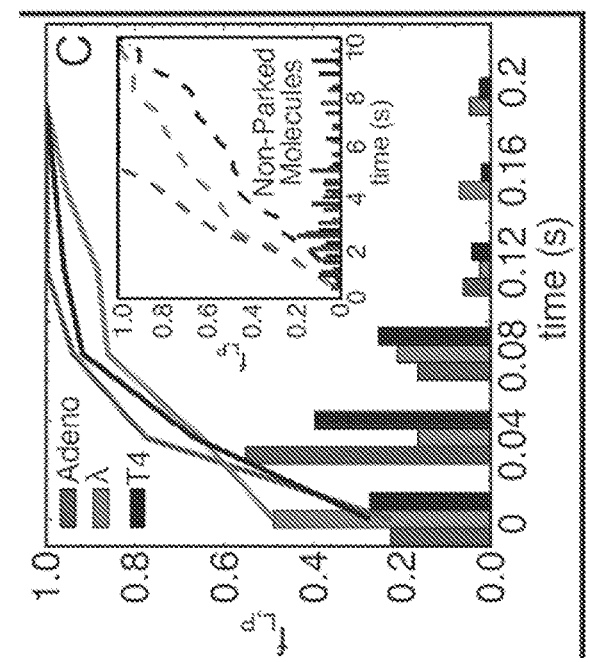
Figure 2C:
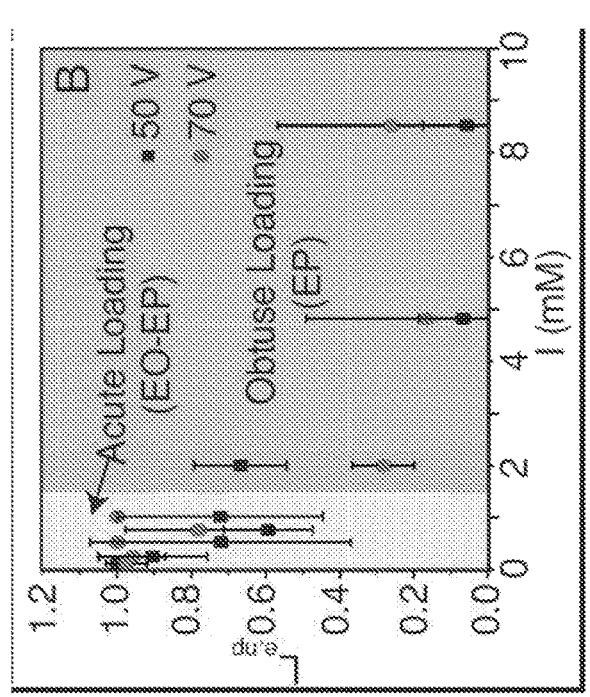
FIG. 2C is a histogram showing frequency of loading parked molecules (main plot) and non-parked molecules (inset) over time, in accordance with an aspect of the present disclosure.
Figure 3A:
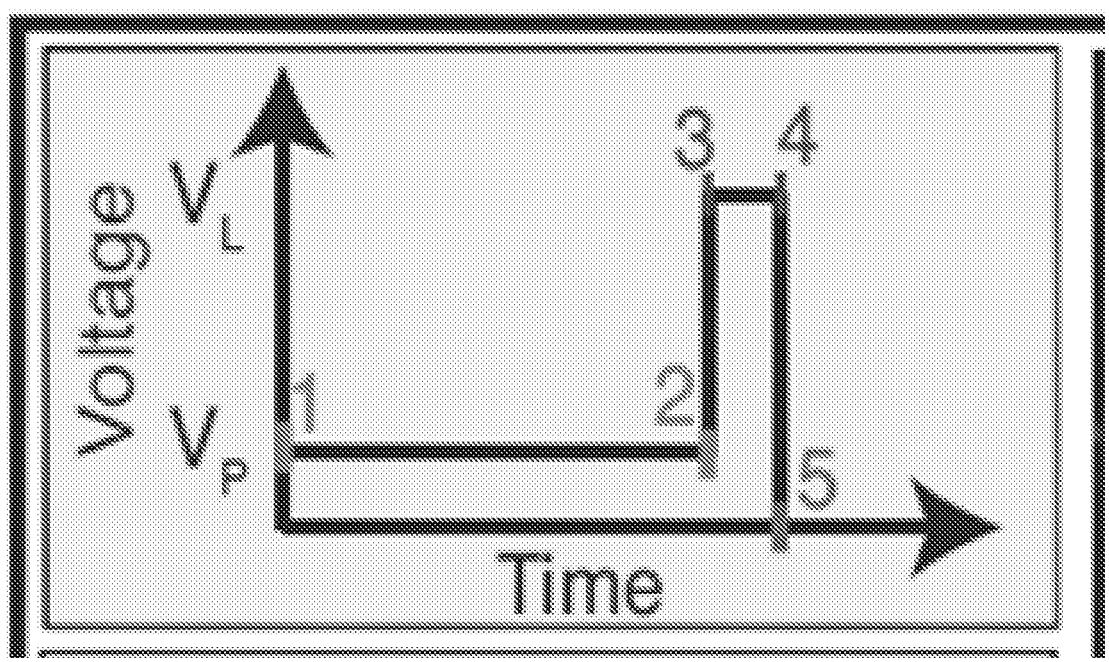
FIG. 3A is a chart illustrating an exemplary power supply routine applied to the system of FIG. 1B, in accordance with an aspect of the present disclosure.

Referring to FIGS. 3A-3E2, an exemplary mode of operation of microfluidic device 10 within the system 200 is illustrated. In the exemplary mode of operation, molecules or particles of interest 50 are shown being parked and loaded into the first secondary nanoslit 102, as well as the plurality of secondary nanoslits, of the microfluidic device 10. It will be understood that this mode of operation is applicable to the loading each of the various primary, secondary, tertiary, and all other nanoslits of the microfluidic device 10 described herein.

As shown in FIG. 3A, the power supply routine is configured to provide a first voltage $V_P$ for a first length of time (between points 1 and 2), a second voltage $V_L$ for a second length of time (between points 3 and 4), and a third voltage $V_O$ for a third length of time (from point 5 to a predetermined point in time). The first voltage $V_P$ and the first length of time are configured to load molecules or particles of interest 50 into associated parking chambers of the microfluidic device 10. The second voltage $V_L$ and the second length of time are configured to load molecules or particles of interest 50 from the associated parking chambers into associated nanoslits that are each connected to one of the associated parking chamber. The third voltage $V_O$ and the third length of time are configured to allow the molecules or particles of interest 50, such as nucleic acid molecules, loaded in the associated nanoslits to have a dumbbell configuration.

Thus, as shown in FIGS. 3B1 and 3B2, prior to applying the first voltage $V_P$, the molecules or particles of interest 50 may be disposed within the secondary microchannel 22, suspended within a buffer filling the device receiving chamber 202. Then, as shown in FIGS. 3C1 and 3C2, the first voltage $V_P$ is applied for the first length of time to load the molecules or particles of interest 50 into the various parking chambers of the device 10. Then, as shown in FIGS. 3D1 and 3D2, the second voltage $V_L$ is applied for the second length of time to load the molecules or particles of interest 50 from the associated parking chambers into associated nanoslits that are each connected to one of the associated parking chamber. Finally, as shown in FIGS. 3E1 and 3E2, the third voltage $V_O$ is applied for the third length of time to allow the molecules or particles of interest 50, which may be nucleic acid molecules, loaded in the associated nanoslits to have a dumbbell configuration.

In some instances, the power supply routine is configured to load molecules into parking chambers under conditions where an electroosmotic force dominates motion of the molecules.

In some instances, the power supply routine is configured to apply a voltage routine that applies a first voltage to load the plurality of molecules or particles of interest 50 into the corresponding parking chambers and applies a second voltage that is greater than a 50% loading efficiency for a first size of molecule and is less than a 50% loading efficiency for a second size of molecule, thereby selectively loading the plurality of nanoslits with a portion of the plurality of molecules or particles of interest 50 having a size distribution that is weighted more heavily toward the first size when compared with the plurality of molecules or particles of interest 50.

Accordingly, in some non-limiting examples, the system 200 comprises the microfluidic device 10 that is configured for isolating the plurality of molecules or particles of interest 50. The microfluidic device 10 includes a plurality of parking chambers and a plurality of nanoslits. Each of the plurality of nanoslits is connected to an associated parking chamber of the plurality of parking chambers. Each of the plurality of parking chambers is connected to an associated nanoslit of the plurality of nanoslits.

The system 200 comprises the at least two electrodes 210, wherein the at least two electrodes 210 are positioned relative to the microfluidic device such that applying a voltage to the at least two electrodes 210 provides at least a portion of the voltage across the plurality of nanoslits. The system 200 further comprises the power supply 204 in electronic communication with the at least two electrodes 210. The system 200 further comprises a power supply controller 206 configured to execute a power supply routine that is configured to selectively load at least a portion of the plurality of parking chambers with one and only one of the plurality of molecules or particles of interest 50 under conditions where motion of the selectively loaded molecules or particles of interest 50 is at least partially aligned with a direction of electroosmotic forces. The power supply routine utilizes (a) a geometry of the microfluidic device relative to the at least two electrodes 210, (b) an ionic strength of an ionic buffer within the microfluidic device 10, and (c) electrostatic or hydrodynamic properties of the microfluidic device and electrostatic or hydrodynamic properties of the plurality of molecules or particles of interest 50.

Accordingly, in some other non-limiting examples, the system 200 comprises the microfluidic device 10 that is configured for isolating a plurality of molecules or particles of interest 50. The microfluidic device 10 includes a plurality of parking chambers and a plurality of nanoslits. Each of the plurality of nanoslits is connected to an associated parking chamber of the plurality of parking chambers. Each of the plurality of parking chambers connected to an associated nanoslit of the plurality of nanoslits. The system 200 further comprises the at least two electrodes 210. The at least two electrodes 210 are positioned relative to the microfluidic device such that applying a voltage to the at least two electrodes 210 provides at least a portion of the voltage across the plurality of nanoslits. The system 200 further comprises the power supply in electronic communication with the at least two electrodes 210. The power supply controller 206 is configured to execute a power supply routine that is configured to apply a voltage routine that applies a first voltage to load the plurality of molecules or particles of interest 50 into the corresponding parking chambers and applies a second voltage that is greater than a 50% loading efficiency for a first size of molecule and is less than a 50% loading efficiency for a second size of molecule, thereby selectively loading the plurality of nanoslits with a portion of the plurality of molecules or particles of interest 50 having a size distribution that is weighted more heavily toward the first size when compared with the plurality of molecules or particles of interest 50.

Figure 9:
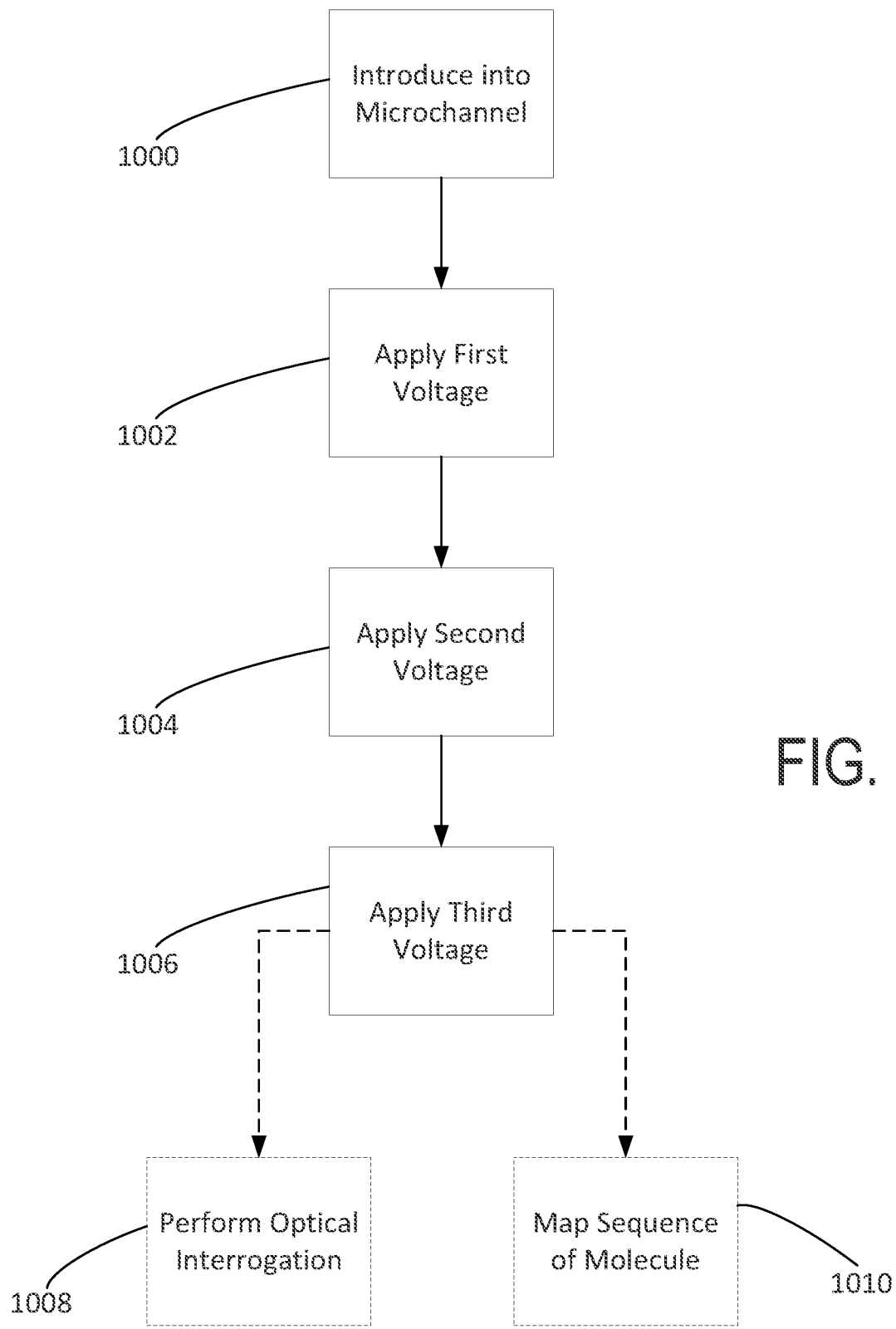
FIG. 9 is a flowchart illustrating a method of loading a plurality of nanoslits with at least a portion of a plurality of molecules or particles of interest, in accordance with an aspect of the present disclosure.

Referring now to FIG. 9, a method of using the system 200 to load a plurality of nanoslits of the microfluidic device 10 with at least a portion of a plurality of molecules or particles of interest 50 is provided below.

The method comprises, at step 1000, introducing the plurality of molecules or particles of interest 50 into a microchannel in communication with a plurality of parking chambers connected to a corresponding plurality of nanoslits, the microchannel, the plurality of parking chambers, and the corresponding plurality of nanoslits each containing an ionic buffer having an ionic strength.

The method further comprises, at step 1002, applying a first voltage for a first length of time, the first voltage is greater than a first voltage threshold and less than a second voltage threshold, thereby causing at least a portion of the plurality of parking chambers to be occupied by one and only one molecule or particle of interest.

The method further comprises, at step 1004, applying a second voltage for a second length of time, the second voltage is greater than the second voltage threshold, thereby causing at least a portion of the plurality of nanoslits to be loaded with one and only one molecule or particle of interest.

The method further comprises, at step 1006, applying a third voltage that is less than the first voltage threshold or zero voltage for a third length of time, thereby causing the molecules or particles of interest 50 loaded in the at least a portion of the plurality of nanoslits to have a dumbbell configuration.

In some instances, the method may further comprise, at step 1008, optically interrogating the molecules having the dumbbell configuration.

In some instances, the method may further comprise, at step 1010, mapping a sequence of the molecules or particles of interest 50. Step 1010 may accordingly comprise mapping a portion of a plurality of the nucleic acid molecules.

In some instances, the first voltage is selected to provide conditions where an electroosmotic force contributes to at least 50% of motion of the molecules. In some instances, the first voltage is selected to provide conditions where motion of molecules moving from the microchannel into the portion of the plurality of parking chambers is at least partially aligned with a direction of electroosmotic forces In some instances, the second voltage and the second length of time are selected to provide a greater than 50% loading efficiency for a first size of molecule and to provide a less than 50% loading efficiency for a second size of molecule, thereby loading the plurality of nanoslits with a portion of the plurality of molecules or particles of interest 50 having a size distribution that is weighted more heavily toward the first size when compared with the entire plurality of molecules or particles of interest 50.

In some instances, the first voltage, the second voltage, the third voltage, or a combination thereof are applied at an angle of between +45° and −45° relative to the at least a portion of the plurality of nanoslits.

In some cases, a monodisperse sample (siz) is utilized. In some cases, a device with mixed geometries can be utilized to synchronously load a disperse population of molecular sizes. In some cases, the device can fractionate a mixture prior to performing the methods described herein.

FIG. 1 show electrostatic confinement and manipulation of DNA: device considerations. (A) Microchannel/nanoslit device schematic (top view): 1.6 μm Height×20 μm Width microchannels (molecule bus) connecting 100 nm H×1 μm W×28.3 μm L nanoslits. Entire device, 0.5 cm×0.5 cm square, comprises 126 microchannels, each one harboring 1,100 nanoslits bounded by molecular gates. (B) Electrostatic potential determined by finite element simulation of the entire device within the buffer chamber. Such simulations guided electrode locations for producing the appropriate field lines within the microchannel/nanoslit device. (C) Microchannel/nanoslit device (imaged by DIC microscopy) is superimposed with arrows showing the direction and magnitude of field lines within device microchannel and nanoslit features (70 V applied). (D) Cartoon (top view) shows the direction and magnitude of the electrokinetic forces for low and high ionic strength conditions. Inset is a SEM micrograph (top view) of a patterned silicon master detailing nanoslits and molecular gates. Micrographs of DNA dumbbells bearing nanocoded labels (red punctates) are shown placed within the device. At low I, electroosmosis (EO, blue arrows) guides molecules along the microchannel, while electrophoresis (EP, yellow arrows) drives them toward the molecular gates. At high I, both directions are dominated by electrophoresis. Molecular trajectories (dotted line) are also drawn. (E) SEM (scanning electron microscopy) image of cup-like Molecular Gate features and dimensions (top view) of a silicon master. Illustration below shows DNA molecules (green) within a microchannel (1.6 μm high). Several molecular gates are shown bearing DNAs threaded into nanoslits (100 nm high), which pass through to the other side to form dumbbells. Note small 1 μm×100 nm slit openings at the bottom of molecular gates. Cross sectional view (inset) depicts intersecting ion distributions (green) surrounding DNA and the nanoslit walls (red). (F)

Perspective drawing showing DNA molecules (green balls/threads) within a microchannel; inset shows ion clouds surround DNA and device walls. Lateral cross-sectional view within a nanoslit, [see (E); Section AA], showing ion clouds, under low and high ionic strength surrounding a DNA molecule (green) and nanoslit (red). At low I, an "electrostatic bottle" is created because ion clouds overlap, electrostatically confining the now stiffened (increased persistence length) DNA molecule. In contrast, high I engenders a short Debye length allowing the molecule to more freely diffuse throughout the entire height of the nanoslit. Furthermore, ionic strength conditions collectively affect the profile of the electroosmotic flow fields, illustrated by arrows, where the maximum velocity depends directly on the ratio between confinement dimensions and Debye length.

FIG. 2 illustrates how DNA parking synchronizes nanoslit loading controlled by ionic strength conditions. (A1 and A2) Green traces show trajectories of adeno DNA molecules traveling through a microchannel, without parking, loading into nanoslits captured by superimposition of 174 image frames (0.03 s interval); device is detailed in FIG. 1. (A1) Yellow arrows indicate overall direction of DNA migration (low ionic strength: 0.51 mM) under electroosmotic and electrophoretic forces. Accumulation of intense fluorescence along the "molecular gate"/microchannel interface (A2), indicates lack of passage through nanoslits. Same conditions, except blue arrows indicate DNA migration dominated by electrophoretic forces under high ionic strength (8.5 mM). (B) Plot shows how loading efficiency, $L_{e,nP}$, or the yield of adeno DNA molecules as imaged being present at a molecular gate that then goes on to load into nanoslits, without a parking step, varies with ionic strength and applied voltage (square wave signals: 0 V to 70 V, or 0 V to 50 V; 0.1 Hz). Error bars are standard deviations on the means; sample size for the experiments ranged from 18-94 molecules. Colors highlight DNA loading regimes: [yellow] acute loading (EO-EP), [green] transition, and [blue] obtuse (EP). (C) Histogram showing the frequency of loading, after parking, $f_{L,P}$, over time, across three DNA sizes: adeno (35.9 kb), lambda (48.5 kb), and T4 (165.6 kb). Inset: loading frequencies, $f_{L,nP}$, for molecules without a parking step; lines represent cumulative frequency for each DNA sample (23-67 measurements). Micrographs show an example of lambda DNA molecules (green) shown parked and loading; white outlines define molecular gates and nanoslit walls.

FIGS. 3B1-3E2 illustrate parking, loading and synchronized formation of T4 DNA dumbbells. Schematic of electrical signal triggering synchronized loading and dumbbell formation of parked DNA molecules into nanoslits. Micrographs, accompanied by cartoons, show T4 (165.6 kb) DNA molecules: (1) Within several microchannels migrating toward the molecular gates ($V_p$=20 V; t=0 s) for parking. (2) A portion of these DNA molecules now reside ($V_p$=20 V; t=70.10 s) within molecular gates, and are now parked. (3-4). Parked molecules are triggered (t=70.32 s) to synchronously load in to the adjoining slits by a short higher voltage pulse (1.0 s; $V_L$=70 V) to form an array of dumbbells (5) (t=74.01 s).

Figure 4:
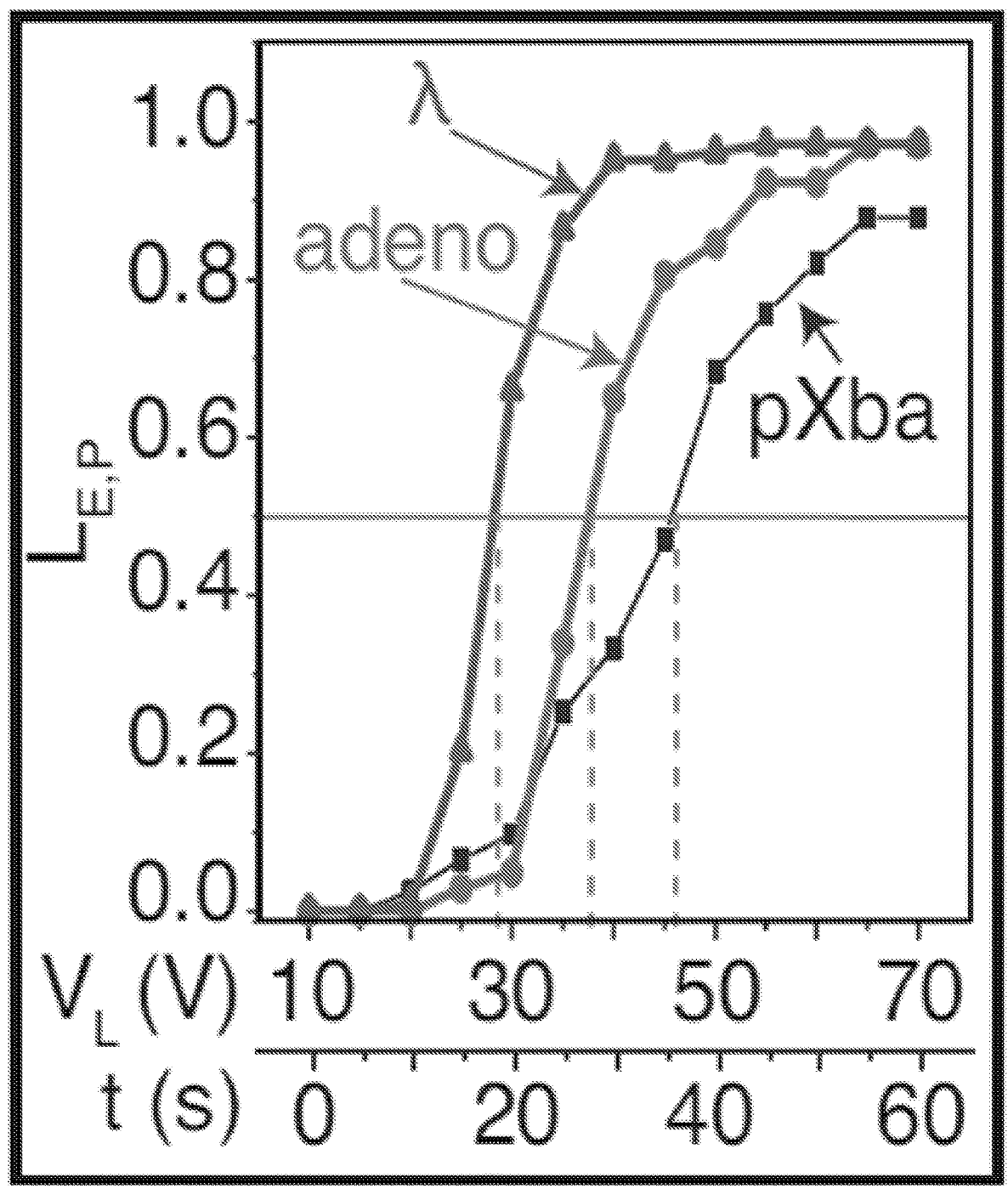
FIG. 4 is a plot of loading efficiency versus voltage (or alternatively, versus time for a stepwise increase in voltage) for different sized nucleic acid molecules of interest, in accordance with an aspect of the present disclosure.

FIG. 4 is a plot illustrating that DNA loading kinetics, after parking, is governed by size and applied voltage. 103-123 molecules were measured per DNA sample and I was fixed at 0.62 mM; molecules were stably parked for 20 s at 10 V before incrementally stepping applied voltage at 5 s intervals, 5 V, from 10 V to 70 V (lower x-axis). Plot shows $L_{E,P}$ vs. $V_L(V)$; $V_L$ is the voltage at which 50% of parked molecules are observed loading into nanoslits (horizontal red line); dashed red lines indicate respective $V_L$ values at $L_{E,P}$=50% for pXba (22.6 kb), adeno (35.9 kb) and λ (48.5 kb) DNA molecules.

Figure 5:
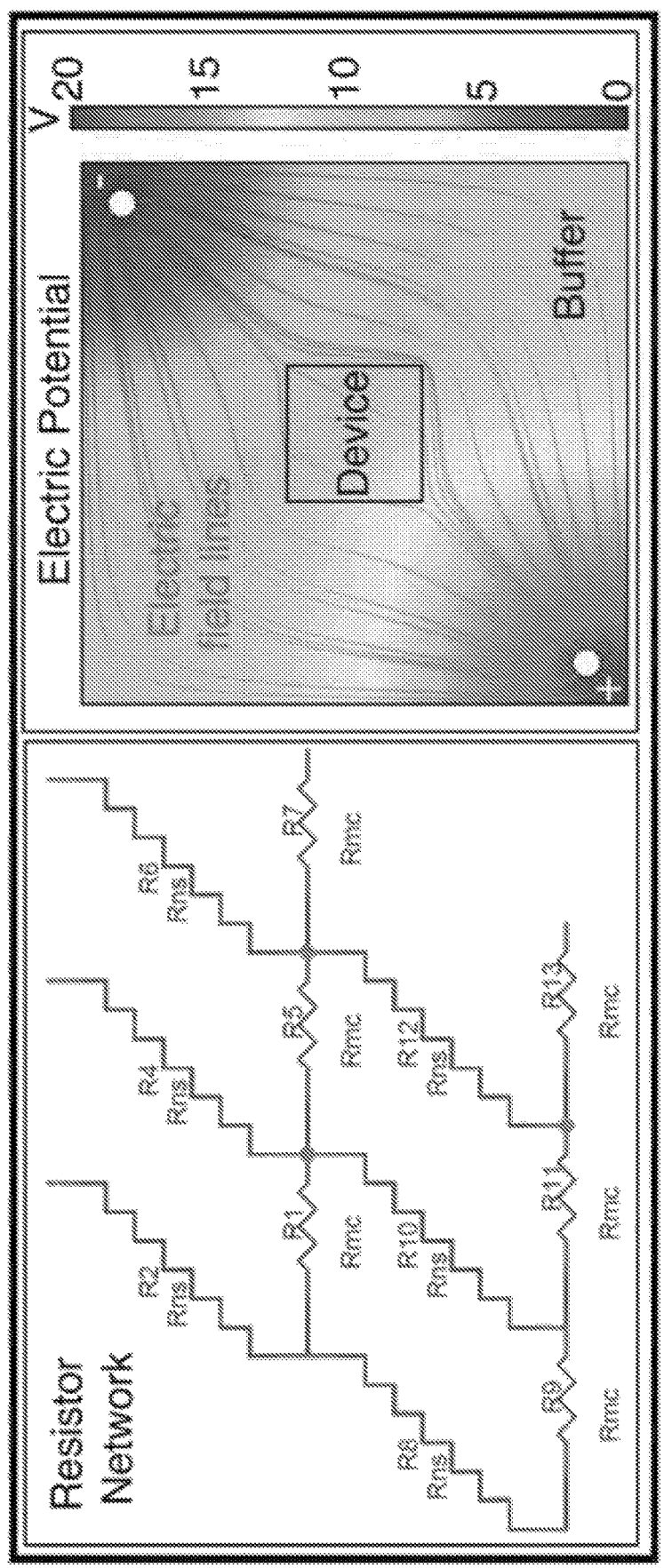
FIG. 5 is a resistor network (left) that approximates the devices described herein and a plot of electrostatic potential (right) for the system described herein, in accordance with an aspect of the present disclosure.

FIG. 5 shows how electric fields are modeled within devices of the present disclosure. LEFT: Resistor network approximation for nanoslit-microchannel network. Unit cell consists of one resistor representing microchannel resistance and one resistor representing the nanoslit. The value of the resistors can be obtained from 1D narrow electrolyte channel model involving Poisson-Boltzmann and Navier-Stokes system of equations. RIGHT: Potential and electric field lines within the device and tank when a potential difference of 20 V is applied.

Figure 6:
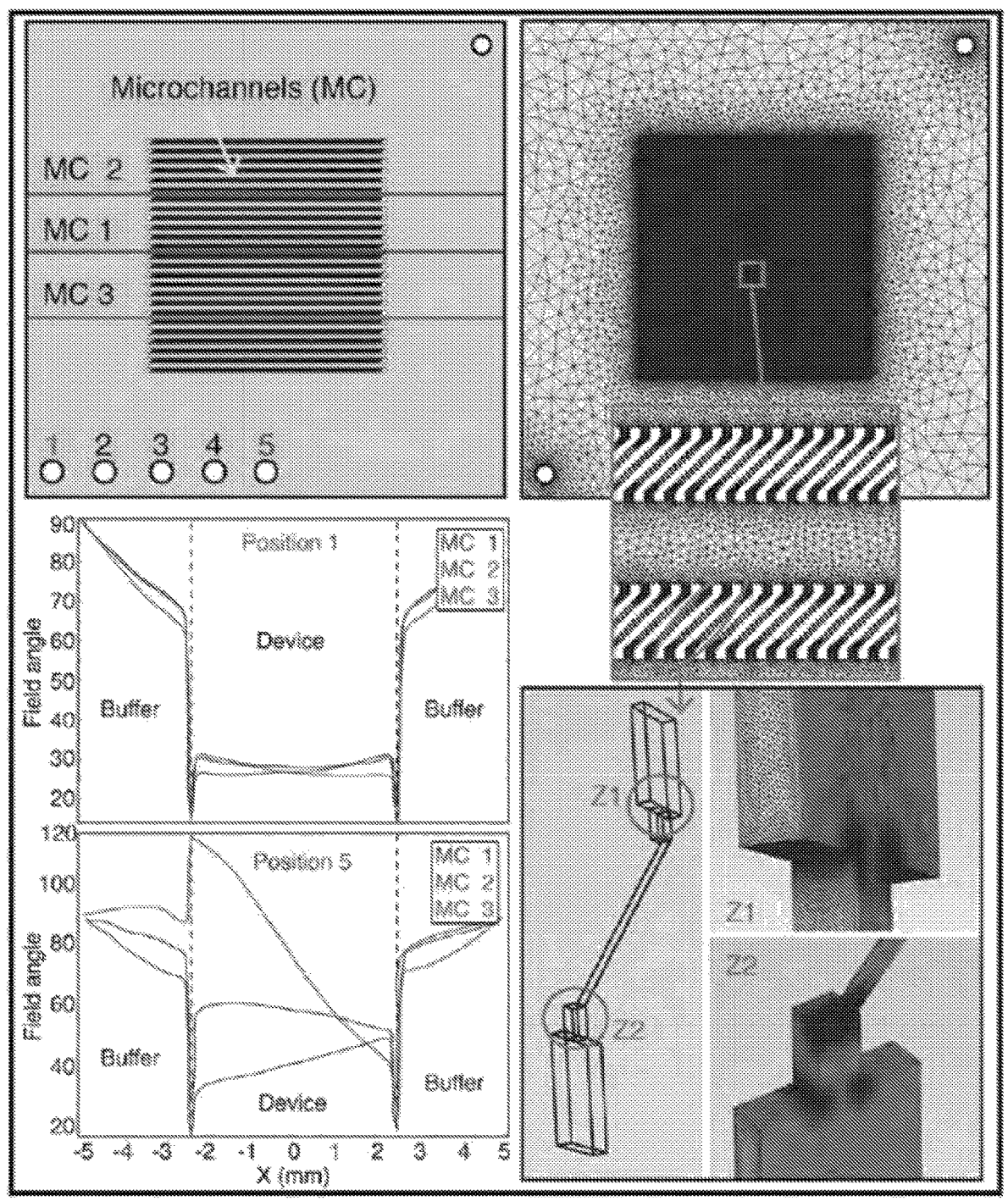
FIG. 6 is an illustration and data relating to electrode placement design, in accordance with an aspect of the present disclosure.

FIG. 6 shows two levels of FE simulations to aid the device design. The device domain is discretized for two- and three-dimensional analysis including the full electrostatic details (potential, field, forces) and Navier-Stokes/Nernst-Planck molecular simulations. Representative meshes for both studies are included. A major component of the design is the angle of the electrical field with respect the microchannel axial direction. This angle controls the direction of the electrophoresis and electroosmotic forces. The location of the electrodes was selected based on this angle, which is shown for the locations 1 and 5 of the electrode.

Figure 7:
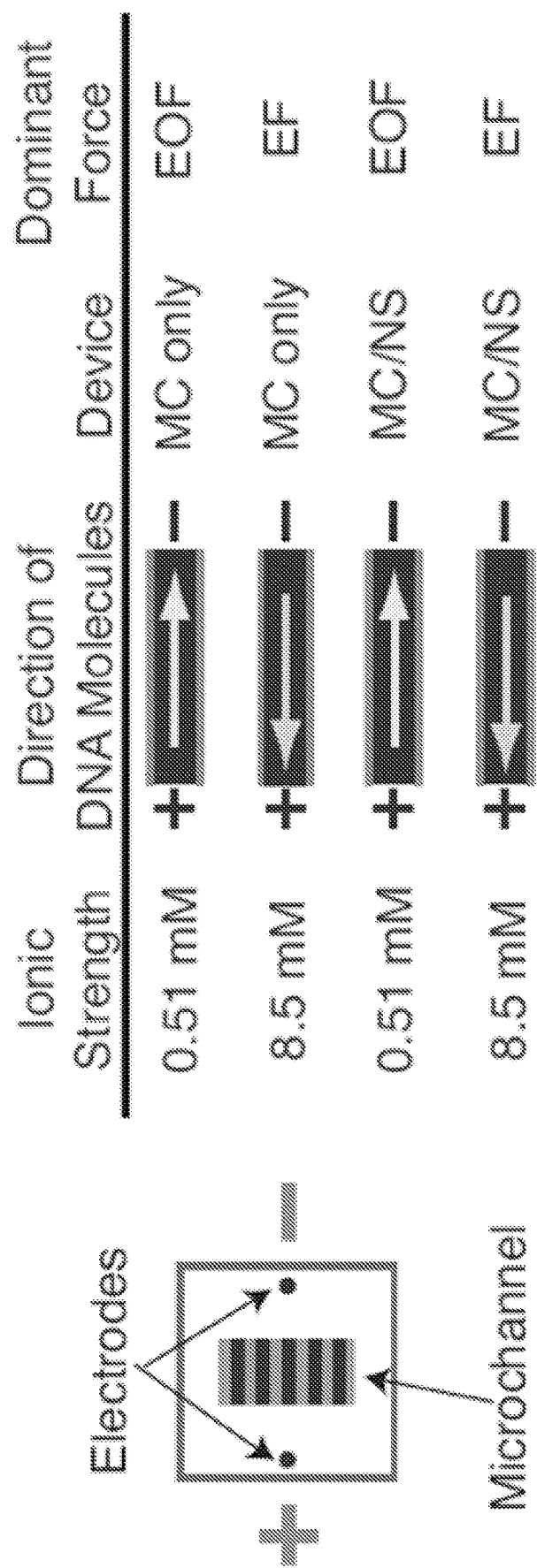
FIG. 7 is an illustration of a "middle electrode" setup and a summary of the dominant forces in molecule transport under different ionic strength conditions, in accordance with an aspect of the present disclosure.

FIG. 7 shows a summary of DNA loading dynamics affected by ionic strength—"middle electrode." Using a middle electrode conformation, migration of adeno DNA molecules (39.5 kb) is dominated by electrophoretic or electroosmotic forces when driven through a microchannel device (MC, without nanoslits; 100 μm wide×3.3 μm tall), or a microchannel-nanoslit device (MC/NS), under different ionic strength conditions: 0.05×TE (I=0.51 mM) or 1×TE (I=8.5 mM). Depending on the ionic strength, electroosmotic or electrophoretic forces will dominate. With the side electrode conformation, the loading regime for low or high ionic strength solutions is acute or obtuse loading, respectively. Acute loading is dominated by electroosmotic flow, while electrophoretic forces dominate obtuse loading. Yellow and blue arrows indicate electroosmotic flow and electrophoretic flow, respectively. White arrows indicate the direction the molecules load into the nanoslit. (N=30 measurements)

FIG. 8 shows loading dynamics of Rhodamine B dye, native, and carboxyl terminated polystyrene microspheres. (a and b) Using a side electrode conformation ("+"; "−"; show electrode orientation and polarity) fluorescently labeled carboxyl terminated (a) or native (b) polystyrene microspheres are electroosmotically driven through the microchannel-nanoslit device. Images in a and b are multiple images superimposed into one image to document the progression of a bead in the microchannel. The time between each image is 0.5 s for a and 0.6 s for b. (c) Neutral Rhodamine B dye migrates electroosmotically in the microchannel of the microchannel-nanoslit device. A DIC (differential interference contrast) image of the microchannel-nanoslit device is overlaid on top of the fluorescence micrographs. A color look-up table is shown to the right of the image. Yellow arrows indicate electroosmotic flow.

Multi-Scale Theoretical Approach Towards Device Design and Functionality.

A comprehensive theoretical study was performed, using multiple length scales, which informed the design and functionalities of the nanofluidic device featuring microchannel and nanoslit geometries (FIG. 1A). Electrostatic conditions, posed by device features and ionic strength conditions, affect both electroosmotic (electrically-driven fluid flows) and electrophoretic forces, controlling DNA migration. These forces were studied using Brownian dynamics (BD), continuum finite element (FE) simulations and arguments from polymer physics, thereby engineering device features that leverage both molecular confinement and electrostatic effects (Materials and Methods). The FE calculations were performed on two levels: a detailed electrostatic study, complemented by full momentum and mass balance simulations (Nernst-Planck/Stokes flow) that explored the micro-channel/cup/nanoslit geometry (FIG. 1E). The electrostatic simulations guided electrode locations through calculation of resulting electric field lines and electrostatic potentials within the device immersed in the surrounding buffer medium. The BD simulations provided insights into enabling electrokinetic effects, within the device, for moving, parking and loading DNA molecules.

Electrical Effects: Electrophoretic Vs. Electroosmotic.

We employ electrostatic considerations for controlling the Debye lengths of both DNA molecules and device features for efficient electrokinetic loading into nanoslits. The Debye length, defined as $\lambda_D^2 = \varepsilon_0 \varepsilon_r k_B T / 2 N_A e^2 I$ (where $k_B$ is the Boltzmann constant, T is the temperature, $N_A$ is Avogadro's number, e is the elementary charge, $\varepsilon_0$ is the vacuum permittivity, $\varepsilon_r$ is the dielectric constant, and I is the ionic strength), determines the length of the electrical double layer (ion cloud) near charged walls and DNA molecules. The unusual design theme here is to foster, rather than hinder electroosmotic flows. However, our thinking is that purely electrophoretic forces may be insufficient for efficient loading molecules into nanoslits decorated by micropillars, which suffer entanglement and not suitable for dealing with very large DNA molecules. FIGS. 1A to 1D show the overall layout of the microfluidic/nanofluidic device. FIG. 1D details the design and functionalities of the device for DNA manipulations using ionic strength regimes engendering electroosmotic flows. The device uses a series of parallel microchannels (a molecule bus) for transporting DNA molecules to the molecular gate features (cup-like structures), which abut each diagonally oriented nanoslit. We expected electroosmotic perturbation of DNA migration due to low ionic strength (I<0.75 mM) buffer conditions and the presence of negatively charged walls of the device (PDMS walls are 02 plasma treated). By increasing the ionic strength (I>2 mM), we see the net direction of migrating DNA molecules reverse, relative to electrode polarity, indicating that the dominating force transitions from electroosmotic to electrophoretic.

FE calculations informed device geometrical design and placements of electrodes within the microscope-mounted buffer tank; multiple systems were simulated for optimization of the effective electric field that would enhance molecular manipulations (parking and loading; see next section). Electrode positions control the field magnitude and direction within the microchannels thereby guiding molecules to gates according to ionic strength, I (as we will describe below). FIG. 1C presents the magnitude and direction of the electric field, calculated by FE, for the electrode configuration in FIG. 1B under 70 V applied at the electrodes. Within the microchannels, the field has a ~5° angle while in the nanoslit it follows the 45° geometrical direction. Importantly, the small cross-sectional area of the nanoslits, compared to microchannels, increases electrical resistance, which increases the electric field strength within that device feature (18-20 V/cm vs. 8-9 V/cm).

We then define DNA migration direction relative to nanoslit features and microchannels as being "acute" (electroosmotic flow), or "obtuse" (electrophoretic) under low (I=0.44-0.89 mM), or high (I=9.0 and 17 mM) ionic strength conditions. FIG. 2A shows time-lapse imaging, rendered as one composite image that reveals migrational trajectories of adeno DNA molecules (35.9 kb) within the device under low and high ionic strength conditions. Remarkably, low ionic strength conditions enable adeno DNA molecules to readily load into the nanoslit features of the device and then exit, as evidenced by sparse occupancies within all device features. In contrast, under high ionic strength conditions, molecules migrate by skirting along the "molecular gate"/microchannel interface, and consequently, do not load, or pass through the nanoslits. FIG. 2B echoes these findings over a range of ionic strength conditions evaluated at two applied voltages (50 V and 70 V) and gauged by loading efficiency into the nanoslits ($L_{e,np}$). At very low ionic strength (I=0.44-0.89 mM) adeno DNA molecules quantitatively load in nanoslits, at 50 V and 70 V, but then loading dramatically decreases, dropping to nearly zero at the highest ionic strength conditions (I=9.0 and 17 mM; 50 V).

Electroosmosis produces a flow-driven force that transports charged molecules towards the similarly-charged electrode; here, the flow field drags DNA molecules, therefore, the electroosmotic force depends on the "Zimm" frictional coefficient ($\zeta_Z \sim R_G \sim L^{3/5}(\omega l_p)^{1/5} \sim L^{3/5}(I^{-3/10})$; where $R_G$, $\omega$ and $l_p$ are the molecule radius of gyration, effective width and persistence length, respectively), the electroosmotic mobility ($\mu_{EO} \sim I^{-1/2}$) and the applied electric field (E): $f_{EO} \sim (\zeta_Z \mu_{EO}) E \sim (I^{-4/5})$ E. In contrast, during DNA electrophoresis, molecules move toward the electrode with opposite charge. Because polyelectrolytes (i.e., DNA) are free draining during electrophoresis, meaning no hydrodynamic shielding, the electrophoretic force is now a function of the "Rouse" frictional coefficient ($\zeta_R \sim 1$). Consequently, the electrophoretic mobility ($\mu_{EP} \sim \ln I^{-1/2}$) and the applied electric field scale as (E): $f_{EP} \sim (\zeta_R \mu_{EP}) E \sim (\ln I^{-1/2}) E$.

It might seem intuitive that obtuse migration of DNA molecules should enhance loading, but we observe a noticeable difference in the loading rate between low and high ionic strength conditions. We attribute this difference to electroosmotic flows within the nanoslits; under high ionic strength conditions "push" molecules away from the molecular gates. Within a nanoslit, the electroosmotic velocity field can be calculated, as a first approximation, from Stokes equations providing an estimate for the characteristic velocity $$u_{eO} \sim 1 - 1/\cosh\left(\frac{H}{\lambda_D}\right);$$

where $u_{EO}$ is the magnitude of the electroosmotic velocity, H is the slit height and $\lambda_D$ is the Debye length. At high ionic strength, the Debye length is small compared to the nanoslit height allowing a fully developed electroosmotic flow within the nanoslit. However, under low ionic strength conditions the flow field will be attenuated by an enlarged Debye length, now comparable to the nanoslit height (FIG. 1E), thereby removing this flow, which prevents loading.

Molecular Gates: Parking, Loading and Synchronized Dumbbell Formation.

The molecular gate dimensions (FIG. 1E)—comparable to the $R_g$ of the DNA coils—are designed for placing and holding an individual molecule at the entrance of each nanoslit. As such, these device features, differing vastly in scale, present support controlled and synchronous loading of DNA molecules into nanoslits. We reasoned that molecules under low applied voltage ($V_P$) would "park" within the molecular gates, and could then be triggered, at high voltage ($V_L$) to synchronously "load" within the nanoslits. We first tested this concept by measuring the loading times for a population of individual molecules sized 35.9 kb, 48.5 kb, and 165.6 kb (FIG. 2C). This plot shows a relatively tight distribution of loading into nanoslits that completes at ~80 ms (80%-90%). In contrast (FIG. 2C inset), non-parked molecules demonstrate a rather broad distribution of loading times that now span seconds because molecules directly enter nanoslits from the microchannels by passing through the molecular gates without parking. Although these loading times (no parking) do not foster synchronous loading across multiple nanoslits, this experiment shows that molecular gates support efficient loading of large DNA molecules into nanoslits, even without the parking step.

Given that parked molecules load within a short period of time (FIG. 2C), we then evaluated this effect for the synchronous formation of dumbbells within multiple slits. FIGS. 3B1-3E2 show T4 DNA molecules moving through microchannels, with $V_P=20$ V, becoming stably parked within molecular gates. Application of a short pulse ($V_L=70$ V) synchronously loads parked molecules in to nanoslits and traps them as dumbbells when V=0. During parking, $V_p$, is carefully selected so that molecules within molecular gates are compressed, as visually judged, but do not load in to adjoining nanoslits. Once parked, the loading voltage, $V_L$, triggers passage into nanoslits through a non-diffusive and fast translocation, fostering synchronized loading. This transition from parked to loaded is sharp for a population of molecules, indicating a kinetic energy barrier in the process (FIG. 2C). The detailed dynamics of loading into nanoslits is complex and will be developed through simulations in another publication. Here, we develop scaling arguments that were used for the design and operation of the device.

Consider a cup (molecular gate) with dimensions W×H×L, where we assume that the cup width (W) and height (H) are equal and L is the length. DNA molecules will park in the cups due to an electric field $E_P$ (driven by the parking voltage, $V_P$), occupying a volume W×H×$L_P$, where $L_P$ is the apparent length of a parked molecule (DNA molecules do not span the entire cup length). There are two main contributions to the free energy of the confined/parked molecules: an entropic contribution given by interactions between the molecule segments and walls $f_{k_BT}$, and the electrostatic contribution $f_{E,cup}$. The entropic contribution can be estimated calculating the number of "de Gennes" blobs and assuming a penalty of $k_BT$ per blob, i.e.

$$f_{k_BT} \sim k_B T \left( \frac{N^{2\nu} b_k^2}{W^2 L_P} \right)^{\frac{1}{3\nu-1}},$$

while the electrostatic contribution is given by $f_{E,cup} \sim NqE_P L_P$. Here, N is the number of $b_k$ segments that form a freely jointed chain, $\nu$ is Flory exponent and q is the molecule segment charge. The total free energy minimum will determine the value of the parked length $L_P$, and an expression for the number of molecule segment per blob is obtained:

$$g \sim \left( \frac{qE_P b_k}{k_B T} \frac{Nb_k^2}{W^2} \right)^{-\frac{1}{3\nu}}.$$

Therefore, the total free energy inside the cup is $f_{cup} \sim k_B T/g$. After the molecules are parked, the loading voltage $V_L$ is applied (with an electric field $E_L$) driving n molecule segments to get inside the nano-slit of height H. The entropic contribution for the free energy of these segments is also of the form $f_{in} \sim k_B T/g_{in}$, where $g_{in} \sim (H/b_k)^{1/\nu}$ is the number of segments inside the nanoslit. The electrostatic contribution for the segments inside is $$f_{E,in} \sim -nqE_L \left( \frac{n}{g_{in}} H \right).$$

The free energy difference, between the energy of molecules in the cup and segments in the nanoslit, will provide an estimate for the free energy barrier $\Delta E_L$. As a first approximation, the energy barrier for loading, $\Delta E_L \sim 1/qE_L H$, is inversely proportional to the total molecule charge q (proportional to DNA molecular weight), the confinement, or device height H and the loading electric field $E_L$. Therefore, longer DNA molecules present higher charge densities within the molecular gate during parking, and should load at a lower voltage than short DNA molecules. It also follows that as the loading voltage is increased, the energy barrier decreases, which works to further enable loading.

Applied Voltage Differentially Loads DNA Molecules as a Function of Size.

Our scaling arguments indicate that loading into nanoslits, after parking, at a given applied voltage should show a pronounced dependence on the size of a DNA coil, with larger molecules triggered to loading before smaller ones. We explored this concept by increasing the applied voltage (10 V-70 V; 5 V per 5 s interval) in a stepwise manner and assessed the loading efficiency, $L_{E,P}$, for different DNA molecule sizes: pXba (22.6 kb), adeno (35.9 kb), and λ(48.5 kb). We define $L_{E,P}$ as the number of molecules that load after parking ($N_{L,P}/N_P$) and $V_L$ as the voltage at which 50% of the parked molecules load in to the nanoslits. FIG. 4 plots $L_{E,P}$ vs. $V_L$(V), showing steep transitions from the parked to loaded state for the larger molecules, λ and adeno; less so for pXba. Differential loading effects are apparent under this voltage stepping scheme: consider that 66% of the parked λ DNA load at 30 V compared to only 5% of the adeno DNA molecules. Analysis of this plot also reveals an inverse linear relationship for size dependent loading, $L_{E,P}(0.5)=-0.77 M_w+67.5$; ($M_w$ in kbp), confirming that larger molecules load before smaller ones. Although direct separation of molecules was not attempted, this plot suggests that excellent size-dependent separations are possible.

Genome Mapping Via DNA Dumbbells: Mesoplasm *Florum*.

We evaluated the effectiveness of the parking and loading scheme for mapping genomes using *M. florum* (793 kb) genomic DNA labeled for Nanocoding [(10); Methods]. Briefly, nick translation places fluorescently labeled nucleotides at nick sites created by Nt.BspQI that are imaged as FRET pairs formed by YOYO-1 (green donor) staining and the covalently incorporated Alexa fluor-647 (red acceptor) moieties. This labeling step effectively barcodes individual DNA molecules through later measurement of punctate spacing, using image processing, to create one restriction map per molecule-termed, "Nmap." Such distance measurements (pixels, nm) are converted into fragment sizes as kilobasepairs by using DNA stretch estimations, determined by alignment using SOMA software [(6); (7); (8); and Methods], which are mediated by ionic strength and the amount of YOYO-1 bound to DNA molecules (8). Accordingly, the pairwise alignment rate of the entire Nmap dataset (906 Nmaps) against the *M. florum* reference map maximized at 86% (781 aligned/906 total) using a stretch of 0.85; FIG. 5 shows these alignments spanning across the entire genome. Briefly, SOMA uses a series of error models, reflecting labeling rates (false and missing) and sizing errors to score and then optimally place Nmaps onto a reference genome. The reference genome is simply an ordered restriction map created in the computer from available sequence. We generate confidence scores (p-values) using an approach similar to that used by Waterman and Vingron for sequence alignments. See, Vingron M & Waterman M S (1994) Sequence alignment and penalty choice. Review of concepts, case studies and implications. *J Mol Biol* 235(1):1-12.

DISCUSSION

We have created an electrostatically-inspired approach for genome analysis through design of a nanofluidic device embracing a series of synergistic functionalities exhibited by both DNA molecules and the device itself. Here, very low ionic strength conditions augment stretching and strategically combine for effective transport and temporal control of molecules loading into nanoslits. These advances empower DNA dumbbells through parking and loading, which greatly enhance DNA stretching, to be synchronously formed and analyzed for mapping *M. florum* using genomic DNA molecules. We accomplished this through the elucidation and harnessing of two major electrostatic effects: (1) Enhanced confinement of DNA molecules within relatively large, easily fabricated nanoslits. (2) Electrokinetic actions using both electroosmotic and electrophoretic forces, which greatly facilitate and synchronize loading DNA molecules into nanoslits via molecular gates.

These device effects and functionalities hinge on controlling the Debye lengths ($\lambda_D$) associated with DNA molecules (polyelectrolyte) and the charged device features by varying buffer ionic strength conditions. Here, high ionic strength solutions (~8 mM) produce compact ion clouds (~1 nm), whereas low ionic strength solutions, ~0.1 mM, generate expansive ion clouds (~30 nm). Accordingly, at low ionic strength, device nanoslit (100 nm high) and DNA (60 nm Debye diameter) Debye layers intersect (FIG. 1F) to enhance DNA confinement and consequent stretching. Low ionic strength conditions also increase the "stiffness," or persistence length of DNA molecules, which is yet another effect that further enhances DNA stretch within the device. This stiffness follows Odijk-Skolnik-Fixman theory ($l_p \sim l_{p,0} + I^{-1}$), where $l_{p,0}$ is the persistence length excluding electrostatic considerations, which governs the average dimension of a DNA random coil, explicitly described by the radius of gyration:

$$(R_G \sim l_p^{\frac{1}{3}}(\lambda_D + \lambda_D \log \lambda_D).$$

Accordingly, increased ionic strength decreases coil dimensions; for example we see that as I increases (0.1 vs. 8.5 mM), $l_p$ shrinks (358 vs. 53 nm), thereby reducing $R_G$ (1.9 vs. 0.7 μm). Importantly, our previous work had shown that increasing DNA persistence length under nanoconfinement greatly increases its stretch: $X/L = 1 - 0.085[(A/l_p)^{2/3} + (B/l_p)^{2/3}]$; where X is the measured molecule length, L is the polymer contour length, and A and B are the slit height and width.

Electrostatic considerations allowed us to engineer a device modality that synchronously loads DNA molecules into nanoslit geometries in ways that portend its broad application. The overall utility of the molecular gate geometry, complemented by low ionic strength conditions, showed usefulness for genome analysis via synchronous dumbbell formation within nanoslits parking/loading, and an almost "digital-like" separation ability (FIG. 4), where under certain conditions, closely sized DNA molecules exhibit either great mobility, or effectively none. In addition, we showed facile entry of large DNA molecules into nanoslits, even without using the parking and loading routine (FIG. 2C).

Nascent systems for genome analysis gain credibility when they demonstrate the potential for high-throughput operation. Although a limited portion of our device was sampled for the complete mapping the *M. florum* genome, the device harbors 138,600 nanoslits, each 28 μm in length. With a total length of almost 4 meters, the device can hold DNA molecules corresponding to ~4 haploid human genome equivalents. Given such capacity, automated data acquisition schemes are easily envisioned where serial dumbbell formation and concerted imaging over occupied portions of the device would enable high-throughput operation.

Methods

Device Design and Fabrication.

Devices fabrication was multistep via standard photolithography and electron beam lithography techniques: (1) Fiduciary marks, UVIII were spin coated (~600 nm) onto a silicon wafer then exposed using a JBX5DII electron beam lithography system (JEOL; CNTech; UW-Madison). Oxygen de-scum process removed organic deposits or residual resist before evaporating metal. A ~20 nm layer of platinum was placed by electron beam evaporation (CNTech; UW-Madison) to promote adhesion between the silicon wafer; a gold layer (~60 nm thick) was then deposited for a high contrast mark for alignment between multiple layers. Sonication (acetone) facilitated liftoff of the excess metal, followed by isopropyl alcohol (IPA) rinse, water rinse and airdrying. (2) SU8 2000.5 photoresist (~250 nm; Micro-Chem, Newton, Mass.) was applied and exposed as boxes over the alignment marks protecting marks against subsequent etching steps. (3) SU8 2000.5 was spin coated (~250 nm) onto a wafer and the nanoslits were exposed, developed using SU8 remover and IPA. SU8 nanoslits were etched into the silicon wafer with CF4 (8 min, 10 mTorr; Unaxis 790, Unaxis Wafer Processing, St. Petersburg, Fla.), placed in a piranha bath (80% H2SO4 and 20% H2O2) for 5 min to remove the residual SU8, and rinsed with water to remove the acid. Finally, the microchannel with molecular gates, aligned with the slits by global and chip fiduciary marks, were exposed by electron beam lithography. SI Methods details silicone replica creation.

Device Setup, Parking, and Loading. Acid cleaned glass coverslips with a PDMS device adhered were affixed to a Plexiglas® holder using paraffin wax. Capillary action loaded device microchannels using a 3 μl solution containing final concentrations of DNA (0.615 ng/μl), YOYO-1 (in water; 0.38 μM), B-mercaptoethanol (3.65%), and POP6 (0.091%; ThermoFisher Scientific). Next, devices were immersed in 2 ml of 0.05×TE buffer (10 mM Tris-HCl, 1 mM EDTA; pH=7.9; solution dilutions checked by conductivity) for 20 minutes before electrokinetic loading of DNA molecules into nanoslits using platinum electrodes inserted into the reservoirs. DNA was loaded into nanoslits via parking and loading using an electrical signal [~20 s: square waveform (20V-70V; 0.025 Hz)] with electrodes 2.5 cm apart. Thusly parked molecules were then synchronously loaded into adjoining nanoslits (70 V using a square wave signal; ~1 s duration).

SI Methods

PDMS Replication of the Master Device. PDMS [poly (dimethylsiloxane), Sylgard 184, Dow Corning, Midland, Mich.] replicas were formed by pouring PDMS with a 10:1 ratio (wt/wt) of pre-polymer to Platinum catalyst and cured at 65° C. for 24 hours. PDMS devices were plasma treated with $O_2$ (100 W, ~0.67 mbar, 36 s, Technics Plasma GMBH 440, Florence, Ky.) to produce hydrophilic channels and stored in ultra pure water for 24 hours. Additionally, the treated devices were sonicated in 0.5 M EDTA (ethylenediaminetetraacetic acid) pH 8.5 for 30 minutes to extract $Pt^+$ ions (present in the PDMS catalyst), because $Pt^+$ ions attenuate YOYO-1/DNA fluorescence by displacing intercalated YOYO-1 with $Pt^+$ (1). The devices were rinsed five times in ultra pure water and rocked at room temperature for each rinse. Finally, PDMS devices were mounted on cleaned glass surfaces as previously described (2).

M. Florum DNA Preparation, Labeling and Mapping.

M. florum genomic DNA were prepared in gel inserts (3), nicked at Nt.BspQI restriction enzyme sites, then labeled by E. coli polymerase I nick translation using fluorochrome-labeled nucleotides (Alexa fluor 647) following our previously reported nanocoding protocol (4). (DNA samples were also restriction digested with SmaI and ApaI for creating populations of linear molecules that would also support complete mapping of the M. florum genome.) Thusly labeled molecules were stained with YOYO-1 and presented as dumbbells (11) via parking (20 V) and loading (70 V; FIG. 3A) within the nanofluidic devices (FIG. 1). Restriction sites, were imaged as red punctuates against a green DNA backbone, revealed by FRET (Fluorescence Resonance Energy Transfer) using laser excitation of the intercalated YOYO-1 dye (donor), which non-radiatively transfers energy to Alexa 647 fluors (acceptor) covalently incorporated within a DNA molecule. FRET imaging advantageously simplifies image acquisition by requiring just one excitation source, while also minimizing background fluorescence from unincorporated fluors (4). A restriction of map, or an "Nmap" of an individual DNA molecule was constructed by distance measurements (pixels) using Image J software (5) between centroids determined at punctates, which labeled restriction sites. Fragment sizes (kb) were then estimated by multiplication of pixel lengths by a conversion factor (kb/pixel), which also provided an apparent DNA stretch (X/L=0.85; full length, X/L=1) after optimization of the pairwise alignment rate of the Nmap dataset (906 Nmaps), using SOMA software (6-8) to the M. florum Nt.BspQI restriction map computed from sequence. The SOMA alignment parameters incorporated expected experimental errors such as sizing, and missing, or spurious punctates and 781/906 (86%) Nmaps were aligned to the M. florum reference map (FIG. 5).

Microscopy and Data Acquisition for Elongated DNAs with Nanoslits.

A Zeiss 135M (63× objective) coupled to an Argon laser (488 nm, Spectra Physics) for excitation was used for imaging YOYO-1 stained DNA molecules. Manual Collect, laboratory software (1), controlled the Hamamatsu Orca-M (Hamamatsu City, Japan) camera for still images, or an Andor iXon EMCCD (Andor Technology Ltd., UK) camera was used to acquire movies during parking and loading. For the collection of molecules bearing punctates undergoing FRET, a filter holder with filters in two different positions: in position one, YOYO-1 excitation (XF3086) and in position two, FRET excitation of Alexa fluor 647 (XF3076; Omega Optical, Inc.) (1).

Electrostatic and Brownian Dynamic Simulations

To guide the design of the device we used for DNA parking and loading within a nanoslit-microchannel network we simulated its electrical characteristics using the following approaches and approximations. The potential distribution across the device is considered by a two-dimensional electrostatic Poisson equation, where the microchannel-nanoslit network is modeled by an anisotropic conductivity tensor and the domain outside of PDMS has isotropic bulk buffer conductivity. Electric current continuity is assumed on buffer-PDMS border and current insulation on the bath/tank walls. Electrodes at diagonal corners of the bath are taken at certain potential difference to each other, about 20 V for parking and 70 V for loading step. The resulting potential distribution within the network represents the average potential growth over many periods of the network and does not capture complex details of microchannel to nanoslit transition through a cup, involving Debye layers and electroosmotic phenomena. In order to derive an anisotropic conductivity tensor of the nanoslit-microchannel network we approximate it as a periodic resistor network in which unit cell consists of just two "resistors": one representing the resistance of a microchannel and one of the nanoslit (FIG. 5). The value of the resistors is obtained using an analytical treatment of a 1D narrow electrolyte channel model involving Poisson-Boltzmann and Navier-Stokes system of equations (9-10).

The network conductivity tensor is given by:

$$\hat{\sigma} = \begin{bmatrix} \dfrac{P_x}{P_y R_m} + \dfrac{L_n \cos^2\alpha}{P_y R_n}, & \dfrac{L_n \sin\alpha \cdot \cos\alpha}{P_y R_n} \\ \dfrac{L_n \sin\alpha \cdot \cos\alpha}{P_x R_n}, & \dfrac{L_n \sin^2\alpha}{P_x R_n} \end{bmatrix}$$

where $P_x$, $P_y$ are the periods of the network in x and y direction respectively, $L_n$ is the length of the nanoslit channel, $R_n$, $R_m$ are resistances of the nanoslit and microchannel segments and $\alpha$ is the nanoslit angle with positive x direction. The 1D problem for the resistances $R_n$, $R_m$ is solved using the finite element method (FEM) thought the COMSOL multi-physics package. Typical potential and electrical current distribution is shown in FIG. 5 right. For instance, for a 10 mm×10 mm device in a 20 mm×20 mm tank filled with 0.5 mM buffer (producing Debye layer length on the order of 30 nm) and an electrode potential difference of 70 V about 4 V drops across the PDMS is expected. The corresponding electrical field within the microchannels is around 8 V/cm.

For a detailed electrostatic study, needed to guide the location of the electrodes and to known the value and direction of the electrostatic forces, a FEM solution is performed, where the Maxwell equations are solved numerically on the complete device. COMSOL Multiphysics package is also used for this task. The domain discretization resulted in simulations with 12.5 million degrees of freedom using second order triangular elements and including 126 microchannels and 138,600 nanoslits. Three set of simulations were carried out, where the location of the electrodes, positive and negative, were changed relative to each other to explore the optimal conditions, i.e. direction of the electric field and the electrostatic forces, that ensure molecular parking and loading.

FIG. 6 shows representative meshes for the two- and three-dimensional FE analysis. In the figure, we include representative meshes for the electrostatic (2D) and the Navier-Stokes/Nernst-Planck (3D) simulations. A major component of the theoretical design is to be able to control, in every microchannel, the electric field angle with respect to the microchannel axial direction. This consideration is fundamental to controlling the direction DNA molecules take under electrophoretic or electroosmotic forces. In the figure, the electrical field angle is plotted as a function of the x-coordinate when the electrodes are in positions 1 and 5. Notice that for position 1, the electric field direction, within the microchannels is between 25° and 30°, allowing an even control of the DNA migration across the entire device. However, if the electrode is located in position 5 the electric field angle dramatically changes from bottom to top; and in some regions the angle is even higher than 90°. Position 1 allows controlled migration and synchronized parking and loading throughout the device. This advantage ensures complete use of the device area portending high-throughput operation. For example, the device used in this work comprises: 128 microchannels×1100 nanoslits×28 µm long nanoslits, which can house DNA molecules at the rate of 2.28 kb/µm (YOYO-1 stained DNA)=8.84 Gb, which is equivalent to 2.8 human genomes pre device loading.

Electroosmotic Flow Experiments with DNAs, Beads, and Rhodamine Dye

Ionic Strength Affects DNA Migration within the Microchannel/Nanoslit Device.

DNA molecules in different ionic strength conditions (IS=0.5 mM (0.05×TE) or 8.5 mM (1×TE); pH=7.9) were used to test how ionic strength conditions affect the electroosmotic flow in microchannels (FIGS. 2A1, 2A2, and 2B). DNA molecules were loaded into the microchannel via capillary flow, the device was immersed in buffer, and then an electric field was applied. Two different devices are utilized in this experiment (FIG. 7): the device described here and a device with only microchannels (100 m wide×3.3 µm high; (2)). The ionic strength was varied to the direction that DNA migration takes to inform the contributions of electroosmotic and electrophoretic flows within microchannels. A voltage of 20 V was applied to the device and molecules were imaged using a SIT camera connected to Pinnacle Studio software. Molecules were analyzed using Image J software to track the centroid position of the molecule. At lower ionic strength environments, the migration in the microchannel is acute—electroosmotic flow dominates. At high ionic strength conditions, electrophoretic forces dominate.

Carboxyl Terminated or Native Polystyrene Beads.

Carboxyl terminated beads (0.11 µm diameter; Molecular Probes, Eugene, Oreg.) and native polystyrene beads (0.11 µm diameter; Polysciences, Warrington, Pa.) were diluted in 0.5 mM NaCl pH=6.4 for subsequent analysis of electroosmotic flow in the microchannel. Beads were loaded into the microchanels through capillary loading then the entire device was immersed in buffer (0.5 mM NaCl pH=6.4), the Plexiglas holder was mounted to the microscope stand, and the power supply was attached to the electrodes. Beads were electrokinetically moved (20 V) within microchannels to check the loading direction: obtuse (dominated by electrophoresis; or, acute (dominated by electroosmosis. Both sets of beads, carboxyl terminated (FIG. 8A) and native polystyrene beads (FIG. 8B), migrated in the microchannel with acute loading (via electroosmotic flow) under low ionic strength, which is in the same direction as the DNA molecules; indicating that electroosmotic flow dominates in the microchannels. The diluted beads, carboxyl terminated or native polystyrene, were imaged in the microchannels using Andor iXon camera with a frame rate ~15 frames/s and tracked overtime using ImageJ (5).

Rhodamine B Dye.

A plug of 0.9 mM Rhodamine B (Thermo Fisher Science, Waltham, Mass.) dye (pH 4.7) was formed within the microchannels to elucidate electroosmotic flow. In order to form a plug, water was introduced into the device then the excess water (water outside the device) was removed, Rhodamine B sample was added to an entrance, on the other side of the device; an aspirator was used to remove some of the water, and finally the device was immersed in water. A voltage (50 V) was applied to the device causing dye migration in microchannels, which were imaged using a SIT 68 camera coupled to a Pinnacle Studio video digitizer, controlled by a computer. Resulting movies were manually analyzed for tracking dye migration patterns (FIGS. 4A-4C). The movement of the Rhodamine towards the anode indicates electroosmotic forces.

Zeta Potential Measurements of Carboxyl Terminated or Native Polystyrene Beads. Native and carboxyl-terminated polystyrene beads (0.11 µm) were purchased from Polyscience and Invitrogen, respectively. The zeta potentials of native polystyrene beads, and carboxylated polystyrene beads were measured and referenced against a standard solution (68+6.8 mV; Malvern Instruments, Worcestershire, UK) using a Zetasizer Nano ZS instrument (Malvern Instruments, Worcestershire, UK). Native and carboxyl-terminated polystyrene beads were diluted using distilled, autoclaved, and filtered water (0.2 µm filter), and then brought up to 0.5 mM NaCl.

The present invention has been described in terms of one or more preferred embodiments, and it should be appreciated that many equivalents, alternatives, variations, and modifications, aside from those expressly stated, are possible and within the scope of the invention.

Referring to FIGS. 1A to 9, the present disclosure also includes the following statements:

1. A microfluidic device comprising:
a primary microchannel defined by primary microchannel walls having a primary distal microchannel surface with a first primary distal microchannel opening, the primary microchannel having a primary microchannel height;
a secondary microchannel defined by secondary microchannel walls having a secondary proximal microchannel surface with a first secondary proximal microchannel opening, the secondary microchannel having a secondary microchannel height;
a first primary nanoslit having a first primary nanoslit height, a first primary nanoslit width, and a first primary nanoslit length; and
a first primary proximal parking chamber having a first primary proximal parking chamber height, a first primary proximal parking chamber width, and a first primary proximal parking chamber length, the first primary nanoslit connected to the first primary proximal parking chamber, the first primary proximal parking chamber connected to the primary microchannel via the first primary distal microchannel opening, the first primary nanoslit in fluid communication with the secondary microchannel via the first secondary proximal microchannel opening.

2. The microfluidic device of statement 1, the microfluidic device further comprising a first primary distal parking chamber having a first primary distal parking chamber height, a first primary distal parking chamber width, and a first primary distal parking chamber length, the first primary nanoslit connected to the first primary distal parking chamber, the first primary distal parking chamber connected to the secondary microchannel via the first secondary proximal microchannel opening.

3. The microfluidic device of statement 1 or 2, wherein the first primary proximal parking chamber has a first primary proximal parking chamber volume of between 1 nm³ and 1 mm³.

4. The microfluidic device of statement 3, wherein the first primary proximal parking chamber volume is between 1 μm³ and 250 μm³.

5. The microfluidic device of any of statements 2 to 4, wherein the first primary distal parking chamber has a first primary distal parking chamber volume of between 1 nm³ and 1 mm³.

6. The microfluidic device of statement 5, wherein the first primary distal parking chamber volume is between 1 μm³ and 250 μm³.

7. The microfluidic device of any of the preceding statements, wherein the first primary proximal parking chamber is configured to be occupied by an integer number of molecules or particles of interest, each having a coiled structure, and to exclude additional molecules or particles of interest from entry.

8. The microfluidic device of statement 7, when the integer number of molecules or particles of interest is a single molecule or particle of interest.

9. The microfluidic device of statement 7 or 8, wherein the integer number of molecules or particles of interest and/or the additional molecules or particles of interest are nucleic acid molecules.

10. The microfluidic device of any of the preceding statements, wherein the first primary proximal parking chamber height is between 1% and 125% of the primary microchannel height.

11. The microfluidic device of any of the preceding statements, wherein the first primary proximal parking chamber height is between 75% and 100% of the primary microchannel height.

12. The microfluidic device of any of statements 2 to 11, wherein the first primary distal parking chamber height is between 1% and 125% of the secondary microchannel height.

13. The microfluidic device of any of statements 2 to 12, wherein the first primary distal parking chamber height is between 75% and 100% of the secondary microchannel height.

14. The microfluidic device of any of the preceding statements, wherein the first primary proximal parking chamber height is between 10 nm and 10 mm, between 100 nm and 50 μm, or between 1.0 μm and 5.0 μm.

15. The microfluidic device of any of the preceding statements, wherein the first primary proximal parking chamber width is 10 nm and 10 mm, between 100 nm and 50 μm, or between 1.0 μm and 5.0 μm.

16. The microfluidic device of any of the preceding statements, wherein the first primary proximal parking chamber length is 10 nm and 10 mm, between 100 nm and 50 μm, or between 1.0 μm and 10.0 μm.

17. The microfluidic device of any of statements 2 to 16, wherein the first primary distal parking chamber height is 10 nm and 10 mm, between 100 nm and 50 μm, or between 1.0 μm and 5.0 μm.

18. The microfluidic device of any of statements 2 to 17, wherein the first primary distal parking chamber width is 10 nm and 10 mm, between 100 nm and 50 μm, or between 1.0 μm and 5.0 μm.

19. The microfluidic device of any of statements 2 to 18, wherein the first primary distal parking chamber length is 10 nm and 10 mm, between 100 nm and 50 μm, or between 1.0 μm and 10.0 μm.

20. The microfluidic device of any of the preceding statements, wherein the first primary nanoslit height is less than 50%, less than 25%, or less than 10% of the first primary proximal parking chamber height.

21. The microfluidic device of any of the preceding statements, wherein the first primary nanoslit height is less than or equal to 100 nm.

22. The microfluidic device of any of the preceding statements, wherein the first primary nanoslit width is less than 50%, less than 25%, or less than 10% of the first primary proximal parking chamber width.

23. The microfluidic device of any of the preceding statements, wherein the first primary nanoslit width is less than or equal to 1 μm.

24. The microfluidic device of any of the preceding statements, wherein the first primary nanoslit length is between 1 μm and 10 mm.

25. The microfluidic device of any of the preceding statements, wherein the first primary nanoslit length is between 10 μm and 100 μm.

26. The microfluidic device of any of the preceding statements, wherein the first primary nanoslit is oriented at an angle of between 10 and 89° relative to a lengthwise axis of the primary microchannel.

27. The microfluidic device of statement 26, wherein the first primary nanoslit is oriented at an angle of between 10° and 80° relative to the lengthwise axis of the primary microchannel.

28. The microfluidic device of statement 27, wherein the first primary nanoslit is oriented at an angle of between 40° and 50° relative to the lengthwise axis of the primary microchannel.

29. The microfluidic device of any of the preceding statements, wherein the first primary nanoslit has a first primary nanoslit cross-sectional area that is less than 25% of a first primary proximal parking chamber cross-sectional area of the first primary proximal parking chamber.

30. The microfluidic device of any of the preceding statements, wherein the primary distal microchannel surface and the secondary proximal microchannel surface are separated by a primary microchannel separation distance of between 1 μm and 10 mm.

31. The microfluidic device of statement 30, wherein the primary microchannel separation distance is between 5 μm and 1 mm or between 10 μm and 100 μm.

32. The microfluidic device of any of the preceding statements, the primary distal microchannel surface further having a second primary distal microchannel opening, the secondary proximal microchannel surface having a second secondary proximal microchannel opening, the microfluidic device further comprising:

a second primary nanoslit having a second primary nanoslit height, a second primary nanoslit width, and a second primary nanoslit length; and a second primary proximal parking chamber having a second primary proximal parking chamber height, a second primary proximal parking chamber width, and a second primary proximal parking chamber length, the second primary nanoslit connected to the second primary proximal parking chamber, the second primary proximal parking chamber connected to the primary microchannel via the second primary distal microchannel opening, the second primary nanoslit in fluid communication with the secondary microchannel via the second secondary proximal microchannel opening.

33. The microfluidic device of statement 32, the microfluidic device further comprising a second primary distal parking chamber having a second primary distal parking chamber height, a second primary distal parking chamber width, and a second primary distal parking chamber length, the second primary nanoslit connected to the second primary distal parking chamber, the second primary distal parking chamber connected to the secondary microchannel via the second secondary proximal microchannel opening.

34. The microfluidic device of any of the preceding statements, the primary distal microchannel surface further having a plurality of primary distal microchannel openings, the secondary proximal microchannel surface having a plurality of secondary proximal microchannel openings, the microfluidic device further comprising:
  a plurality of primary nanoslits; and
  a plurality of primary proximal parking chambers, each of the plurality of primary proximal nanoslits connected to a respective one of the plurality of primary proximal parking chambers, each of the plurality of primary proximal parking chambers connected to the primary microchannel via a respective one of the plurality of primary distal microchannel openings, each of the plurality of primary nanoslits in fluid communication with the secondary microchannel via a respective one of the plurality of secondary proximal microchannel openings.

35. The microfluidic device of statement 34, the microfluidic device further comprising a plurality of primary distal parking chambers, each of the plurality of primary nanoslits connected to a respective one of the plurality of primary distal parking chambers, each of the plurality of primary distal parking chambers connected to the second microchannel via a respective one of the plurality of secondary proximal microchannel openings.

36. The microfluidic device of statement 34 or 35, wherein the second primary proximal parking chamber, the second primary distal parking chamber, one or more of the plurality of primary proximal parking chambers, or one or more of the plurality of primary distal parking chambers has a parking chamber volume of between 1 $nm^3$ and 1 $mm^3$ or between 1 $\mu m^3$ and 250 $\mu m^3$.

37. The micro-fluid device of any of statements 34 to 36, wherein each of the plurality of primary proximal parking chambers or each of the plurality of primary distal parking chambers is configured to be occupied by an integer number of molecules or particles of interest or a single molecule or particle of interest in a coiled structure and to exclude additional molecules or particles of interest from entry.

38. The micro-fluid device of any of statements 34 to 37, wherein the plurality of primary proximal parking chambers each has a primary proximal parking chamber height of between 1% and 125% or between 75% and 100% of the primary microchannel height.

39. The micro-fluid device of any of statements 35 to 38, wherein the plurality of primary distal parking chambers has a primary distal parking chamber height of between 1% and 125% or between 75% and 100% of the secondary microchannel height.

40. The micro-fluid device of any of statements 34 to 39, wherein the plurality of primary proximal parking chambers each has a primary proximal parking chamber height of 10 nm and 10 mm, between 100 nm and 50 $\mu m$, or between 1.0 $\mu m$ and 5.0 $\mu m$.

41. The micro-fluid device of any of statements 34 to 40, wherein the plurality of primary proximal parking chambers each has a primary proximal parking chamber width of 10 nm and 10 mm, between 100 nm and 50 $\mu m$, or between 1.0 $\mu m$ and 5.0 $\mu m$.

42. The micro-fluid device of any of statements 34 to 41, wherein the plurality of primary proximal parking chambers each has a primary proximal parking chamber length of 10 nm and 10 mm, between 100 nm and 50 $\mu m$, or between 1.0 $\mu m$ and 10.0 $\mu m$.

43. The micro-fluid device of any of statements 35 to 42, wherein the plurality of primary distal parking chambers each has a primary distal parking chamber height of between 10 nm and 10 mm, between 100 nm and 50 $\mu m$, or 1.0 $\mu m$ and 5.0 $\mu m$.

44. The micro-fluid device of any of statements 35 to 43, wherein the plurality of primary distal parking chambers each has a primary distal parking chamber width of between 10 nm and 10 mm, between 100 nm and 50 $\mu m$, or 1.0 $\mu m$ and 5.0 $\mu m$.

45. The micro-fluid device of any of statements 35 to 44, wherein the plurality of primary distal parking chambers each has a primary distal parking chamber length of between 10 nm and 10 mm, between 100 nm and 50 $\mu m$, or 1.0 $\mu m$ and 10.0 $\mu m$.

46. The micro-fluid device of any of statements 34 to 45, wherein each of the plurality of primary nanoslits has a primary nanoslit height of less than 50%, less than 25%, or less than 10% of a corresponding primary proximal parking chamber height for the respective one of the plurality of primary proximal parking chambers to which each of the plurality of primary nanoslits is connected.

47. The micro-fluid device of statement 46, wherein the primary nanoslit height is less than or equal to 100 nm.

48. The micro-fluid device of any of statements 34 to 47, wherein each of the plurality of primary nanoslits has a primary nanoslit width of less than 50%, less than 25%, or less than 10% of a corresponding primary proximal parking chamber width for the respective one of the plurality of primary proximal parking chambers to which each of the plurality of primary nanoslits is connected.

49. The micro-fluid device of statement 48, wherein the primary nanoslit width is less than or equal to 1 $\mu m$.

50. The micro-fluid device of any of statements 34 to 49, wherein each of the plurality of primary nanoslits has a primary nanoslit length of between 1 $\mu m$ and 10 mm or between 10 $\mu m$ and 100 $\mu m$.

51. The micro-fluid device of any of statements 34 to 50, wherein each of the plurality of primary nanoslits is oriented at an angle of between 1° and 89°, between 10° and 80°, or between 40° and 50° relative to a lengthwise axis of the primary microchannel.

52. The micro-fluid device of any of statements 34 to 51, wherein each of the plurality of primary nanoslits has a primary nanoslit cross-sectional area that is less than 25% of a primary proximal parking chamber cross-sectional area of the respective one of the plurality of primary proximal parking chambers to which each of the plurality of primary nanoslits is connected.

53. The micro-fluid device of any of statements 34 to 52, wherein the plurality of primary nanoslits are substantially parallel with one another.

54. The micro-fluid device of any of statements 34 to 53, wherein the plurality of primary nanoslits are substantially the same length.

55. The micro-fluid device of any of statements 34 to 57, wherein the plurality of primary nanoslits have a statistical distribution of different lengths.

56. The micro-fluid device of any of statements 34 to 58, wherein the plurality of primary proximal parking chambers are separated by a primary parking chamber separation distance of between 1 nm and 1 mm, between 100 nm and 100 µm, or between 1 µm and 25 µm.

57. The micro-fluid device of any of statements 34 to 56, wherein the plurality of primary nanoslits include at least 100 primary nanoslits.

58. The micro-fluid device of any of statements 34 to 57 wherein the plurality of primary nanoslits include at least 500 nanoslits.

59. The micro-fluid device of any of statements 34 to 58 wherein the plurality of primary nanoslits include at least 1000 nanoslits.

60. The microfluidic device of any of the preceding statements, the secondary microchannel walls having a secondary distal microchannel surface with a first secondary distal microchannel opening, the microfluidic device further comprising:
a tertiary microchannel defined by tertiary microchannel walls having a tertiary proximal microchannel surface with a first tertiary proximal microchannel opening, the tertiary microchannel having a tertiary microchannel height;
a first secondary nanoslit having a first secondary nanoslit height, a first secondary nanoslit width, and a first secondary nanoslit length; and
a first secondary proximal parking chamber having a first secondary proximal parking chamber height, a first secondary proximal parking chamber width, and a first secondary proximal parking chamber length, the first secondary nanoslit connected to the first secondary proximal parking chamber, the first secondary proximal parking chamber connected to the primary microchannel via the first secondary distal microchannel opening, the first secondary nanoslit in fluid communication with the third microchannel via the first tertiary proximal microchannel opening.

61. The microfluidic device of statement 60, the microfluidic device further comprising a first secondary distal parking chamber having a first secondary distal parking chamber height, a first secondary distal parking chamber width, and a first secondary distal parking chamber length, the first secondary nanoslit connected to the first secondary distal parking chamber, the first secondary distal parking chamber connected to the tertiary microchannel via the first tertiary proximal microchannel opening.

62. The microfluidic device of statement 60 or 61, the secondary distal microchannel surface further having a plurality of secondary distal microchannel openings, the tertiary proximal microchannel surface having a plurality of tertiary proximal microchannel openings, the microfluidic device further comprising:
 a plurality of secondary nanoslits; and
 a plurality of secondary proximal parking chambers, each of the plurality of secondary proximal nanoslits connected to a respective one of the plurality of secondary proximal parking chambers, each of the plurality of secondary proximal parking chambers connected to the secondary microchannel via a respective one of the plurality of secondary distal microchannel openings, each of the plurality of primary nanoslits in fluid communication with the tertiary microchannel via a respective one of the plurality of tertiary proximal microchannel openings.

63. The microfluidic device of statement 62, the microfluidic device further comprising a plurality of secondary distal parking chambers, each of the plurality of secondary nanoslits connected to a respective one of the plurality of secondary distal parking chambers, each of the plurality of secondary distal parking chambers connected to the tertiary microchannel via a respective one of the plurality of tertiary proximal microchannel openings.

64. The microfluidic device of any of the preceding statements, the microfluidic device further comprising:
 a plurality of microchannels, each of the plurality of microchannels defined by microchannel walls having a distal microchannel surface with a plurality of distal microchannel openings, the microchannel walls having a proximal microchannel surface with a plurality of proximal microchannel openings;
 a series of pluralities of nanoslits;
 a series of pluralities of proximal parking chambers; and
 wherein each of the nanoslits in the series of pluralities of nanoslits is connected to a respective proximal parking chamber of the series of pluralities of proximal parking chambers,
 wherein each of the proximal parking chambers in the series of pluralities of proximal parking chambers is connected to a respective proximal microchannel of the plurality of microchannels via a respective proximal microchannel opening of the plurality of proximal microchannel openings,
 wherein each of the nanoslits in the series of pluralities of nanoslits is in fluid communication with a respective distal microchannel via a respective distal microchannel opening of the plurality of distal microchannel openings, and
 wherein the respective distal microchannel neighbors the respective proximal microchannel.

65. The microfluidic device of statement 64, the microfluidic device further comprising:
 a series of pluralities of distal parking chambers,
 wherein each of the nanoslits in the series of pluralities of nanoslits is connected to a respective distal parking chamber of the series of pluralities of distal parking chambers,
 wherein each of the distal parking chambers in the series of pluralities of distal parking chambers is connected to the respective distal microchannel of the plurality of microchannels.

66. The microfluidic device of statement 64 or 65, wherein the plurality of microchannels are open-ended.

67. The microfluidic device of any of statements 64 to 66, wherein each of the plurality of microchannels are evenly spaced.

68. The microfluidic device of any of statements 64 to 67, wherein each of the plurality of microchannels are spaced by a statistical distribution of different distances.

69. The microfluidic device of any of statements 64 to 68, the microfluidic device further comprising:
 a terminal microchannel defined by terminal microchannel walls having a terminal proximal microchannel surface with a plurality of terminal proximal microchannel openings, wherein the first microchannel and the terminal microchannel are positioned at opposite ends of the plurality of microchannels, the plurality of microchannels including a penultimate microchannel that is nearest to the terminal microchannel, the penultimate microchannel defined by penultimate microchannel walls having a penultimate distal microchannel surface with a plurality of penultimate distal microchannel openings;
 a plurality of terminal nanoslits;
 a plurality of terminal proximal parking chambers; and
 a plurality of terminal distal parking chambers, wherein each of the plurality of terminal nanoslits is connected to a respective terminal proximal parking chamber of the plurality of terminal proximal parking chambers, wherein each of the plurality of terminal nanoslits is connected to a respective terminal distal parking chamber of the plurality of terminal distal parking chambers, wherein each of the plurality of terminal proximal parking chambers is connected to the penultimate microchannel via a respective one of the plurality of penultimate distal microchannel openings, and wherein each of the plurality of terminal distal parking chambers is connected to the terminal microchannel via a respective one of the plurality of terminal proximal microchannel openings.

70. The microfluidic device of statement 69, wherein the first microchannel and the terminal microchannel are in fluid communication.

The microfluidic device of any of the preceding statements, wherein at least 50%, at least 75%, or at least 90% of all nanoslits within the microfluidic device are occupied by one and only one molecule or particle of interest or nucleic acid molecule of interest.

71. A system comprising:
the microfluidic device according to any of the preceding statements;
a device receiving chamber comprising a device orienting portion and at least two electrodes, the device orienting portion configured to receive the microfluidic device and reproducibly orient the microfluidic device relative to the at least two electrodes;
a power supply in electronic communication with the at least two electrodes; and
a power supply controller configured to execute a power supply routine.

72. The system of statement 71, the system further comprising a heater or a cooler configured to heat or cool liquid within the microfluidic device and/or within the device receiving chamber.

73. The system of statement 71 or 72, the system further comprising a temperature measurement device configured to measure a temperature of fluid within the microfluidic device and/or the device receiving chamber.

74. The system of any of statements 71 to 73, the system further comprising a spectrometer configured to optically interrogate molecules located in the microfluidic device.

75. The system of statement 74, wherein the spectrometer has sufficient spatial resolution to distinguish between molecules located in adjacent nanoslits.

76. The system of statement 74 or 75, wherein the spectrometer is configured to monitor an occupancy status of one or more parking chambers and/or one or more nanoslits.

77. The system of any of statements 74 to 76, wherein the spectrometer is a fluorescence microscope.

78. The system of any of statements 71 to 77, the system further comprising a user input.

79. The system of any of statements 71 to 78, wherein the power supply controller is programmed with or configured to receive nucleic acid electrostatic or hydrodynamic information regarding molecules or particles of interest, microfluidic device electrostatic or hydrodynamic information regarding the microfluidic device, buffer ionic strength information regarding a buffer of interest, or a combination thereof.

80. The system of any of statements 71 to 79, wherein the power supply routine is configured to provide a first voltage for a first length of time, a second voltage for a second length of time, and a third voltage for a third length of time, wherein the first voltage and the first length of time are configured to load molecules into associated parking chambers, wherein the second voltage and the second length of time are configured to load molecules from the associated parking chambers into associated nanoslits that are each connected to one of the associated parking chamber, and wherein the third voltage and the third length of time are configured to allow the nucleic acid molecules loaded in the associated nanoslits to have a dumbbell configuration.

81. The system of any of statements 71 to 80, wherein the power supply routine is configured to load molecules into parking chambers under conditions where an electroosmotic force dominates motion of the molecules.

82. The system of any of statements 71 to 81, wherein the power supply routine is configured to apply a voltage routine that applies a first voltage to load the plurality of molecules or particles of interest into the corresponding parking chambers and applies a second voltage that is greater than a 50% loading efficiency for a first size of molecule and is less than a 50% loading efficiency for a second size of molecule, thereby selectively loading the plurality of nanoslits with a portion of the plurality of molecules or particles of interest having a size distribution that is weighted more heavily toward the first size when compared with the plurality of molecules or particles of interest.

83. A system comprising:
a microfluidic device configured for isolating a plurality of molecules or particles of interest, the microfluidic device including a plurality of parking chambers and a plurality of nanoslits, each of the plurality of nanoslits connected to an associated parking chamber of the plurality of parking chambers, each of the plurality of parking chambers connected to an associated nanoslit of the plurality of nanoslits;
at least two electrodes, wherein the at least two electrodes are positioned relative to the microfluidic device such that applying a voltage to the at least two electrodes provides at least a portion of the voltage across the plurality of nanoslits;
a power supply in electronic communication with the at least two electrodes; and
a power supply controller configured to execute a power supply routine that is configured to selectively load at least a portion of the plurality of parking chambers with one and only one of the plurality of molecules or particles of interest under conditions where motion of the selectively loaded molecules or particles of interest is at least partially aligned with a direction of electroosmotic forces, the power supply routine utilizing (a) a geometry of the microfluidic device relative to the at least two electrodes, (b) an ionic strength of an ionic buffer within the microfluidic device, and (c) electrostatic or hydrodynamic properties of the microfluidic device and electrostatic or hydrodynamic properties of the plurality of molecules or particles of interest.

84. A system comprising:
a microfluidic device configured for isolating a plurality of molecules or particles of interest, the microfluidic device inlcuding a plurality of parking chambers and a plurality of nanoslits, each of the plurality of nanoslits connected to an associated parking chamber of the plurality of parking chambers, each of the plurality of parking chambers connected to an associated nanoslit of the plurality of nanoslits;
at least two electrodes, wherein the at least two electrodes are positioned relative to the microfluidic device such that applying a voltage to the at least two electrodes provides at least a portion of the voltage across the plurality of nanoslits;

a power supply in electronic communication with the at least two electrodes; and a power supply controller configured to execute a power supply routine that is configured to apply a voltage routine that applies a first voltage to load the plurality of molecules or particles of interest into the corresponding parking chambers and applies a second voltage that is greater than a 50% loading efficiency for a first size of molecule and is less than a 50% loading efficiency for a second size of molecule, thereby selectively loading the plurality of nanoslits with a portion of the plurality of molecules or particles of interest having a size distribution that is weighted more heavily toward the first size when compared with the plurality of molecules or particles of interest.

85. A method of loading a plurality of nanoslits with at least a portion of a plurality of molecules or particles of interest, the method comprising:

introducing the plurality of molecules or particles of interest into a microchannel in communication with a plurality of parking chambers connected to a corresponding plurality of nanoslits, the microchannel, the plurality of parking chambers, and the corresponding plurality of nanoslits each containing an ionic buffer having an ionic strength;

applying a first voltage for a first length of time, the first voltage is greater than a first voltage threshold and less than a second voltage threshold, thereby causing at least a portion of the plurality of parking chambers to be occupied by one and only one molecule or particle of interest;

applying a second voltage for a second length of time, the second voltage is greater than the second voltage threshold, thereby causing at least a portion of the plurality of nanoslits to be loaded with one and only one molecule or particle of interest; and applying a third voltage that is less than the first voltage threshold or zero voltage for a third length of time, thereby causing the molecules or particles of interest loaded in the at least a portion of the plurality of nanoslits to have a dumbbell configuration.

86. The method of statement 85, the method further comprising optically interrogating the molecules having the dumbbell configuration.

87. The method of statement 85 or 86, the method further comprising mapping a sequence of the molecules.

88. The method of any of statements 85 to 87, wherein the first voltage is selected to provide conditions where an electroosmotic force contributes to at least 50% of motion of the molecules.

89. The method of any of statements 85 to 88, wherein the second voltage and the second length of time are selected to provide a greater than 50% loading efficiency for a first size of molecule and to provide a less than 50% loading efficiency for a second size of molecule, thereby loading the plurality of nanoslits with a portion of the plurality of molecules or particles of interest having a size distribution that is weighted more heavily toward the first size when compared with the entire plurality of molecules or particles of interest.

90. The method of any of statements 85 to 89, wherein the first voltage, the second voltage, the third voltage, or a combination thereof are applied at an angle of between +45° and −45° relative to the at least a portion of the plurality of nanoslits.

91. The method of any of statements 85 to 90, the method performed using the device of any of statements 1 to 0 or the system of any of statements 71 to 84.

We claim:

1. A method of loading a plurality of nanoslits with at least a portion of a plurality of molecules or particles of interest, the method comprising:
    a) introducing the plurality of molecules or particles of interest into a microchannel in communication with a plurality of parking chambers connected to a corresponding plurality of nanoslits, the microchannel, the plurality of parking chambers, and the corresponding plurality of nanoslits each containing an ionic buffer having an ionic strength;
    b) applying, for a first time interval, a first voltage greater than a first voltage threshold and less than a second voltage threshold, thereby causing at least a portion of the plurality of parking chambers to be occupied by one and only one molecule or particle of interest;
    c) applying, for a second time interval, a second voltage greater than the second voltage threshold, thereby causing at least a portion of the plurality of nanoslits to be loaded with one and only one molecule or particle of interest from the at least a portion of the plurality of parking chambers; and
    d) applying, for a third time interval, a third voltage less than the first voltage threshold or zero voltage, thereby causing the molecules or particles of interest loaded in the at least a portion of the plurality of nanoslits to assume a dumbbell configuration.

2. The method of claim 1, wherein the first voltage, the first time interval, the second voltage, the second time interval, the third voltage, the third time interval, or a combination thereof are selected such that at least 50% of the plurality of molecules or particles of interest introduced into the microchannel load into the nanoslits and assume a dumbbell configuration.

3. The method of claim 1, the method further comprising:
    e) optically interrogating at least a portion of the plurality of molecules or particles of interest.

4. The method of claim 1, wherein the molecules or particles of interest are nucleic acid molecules.

5. The method of claim 4, the method further comprising mapping a portion of a plurality of the nucleic acid molecules.

6. The method of claim 1, wherein the first voltage is selected to provide conditions where motion of molecules moving from the microchannel into the portion of the plurality of parking chambers is at least partially aligned with a direction of electroosmotic forces.

7. The method of claim 1, wherein the second voltage and the second time interval are selected to provide a greater than 50% loading efficiency for a first size of molecule and to provide a less than 50% loading efficiency for a second size of molecule, thereby loading the plurality of nanoslits with a portion of the plurality of molecules or particles of interest having a size distribution weighted more heavily toward the first size when compared with the entire plurality of molecules or particles of interest.

8. The method of claim 1, wherein the first voltage, the second voltage, the third voltage, or a combination thereof are applied at an angle of between +45° and −45° relative to the at least a portion of the plurality of nanoslits.

9. A system comprising:
    a microfluidic device configured for isolating a plurality of molecules or particles of interest, the microfluidic device including a plurality of parking chambers and a plurality of nanoslits, each of the plurality of nanoslits connected to an associated parking chamber of the plurality of parking chambers, each of the plurality of parking chambers connected to an associated nanoslit of the plurality of nanoslits;

at least two electrodes, wherein the at least two electrodes are positioned relative to the microfluidic device such that applying a voltage to the at least two electrodes provides at least a portion of the voltage across the plurality of nanoslits;

a power supply in electronic communication with the at least two electrodes; and a power supply controller configured to execute a power supply routine, wherein the power supply routine is configured to do one or more of the following:

to apply a first voltage for a first time interval, a second voltage for a second time interval, and a third voltage for a third time interval, wherein the first voltage and the first time interval are configured to cause at least a portion of the plurality of parking chambers to be occupied by one and only one molecule or particle of interest, wherein the second voltage and the second time interval are configured to cause at least a portion of the plurality of nanoslits to be loaded with one and only one molecule or particle of interest from the at least a portion of the plurality of parking chambers, and wherein the third voltage and the third time interval are configured to allow the molecules or particles of interest loaded in the at least a portion of the plurality of nanoslits to assume a dumbbell configuration, to selectively load the at least a portion of the plurality of parking chambers with one and only one of the plurality of molecules or particles of interest under conditions where motion of the selectively loaded molecules or particles of interest is at least partially aligned with a direction of electroosmotic forces, the power supply routine utilizing (a) a geometry of the microfluidic device relative to the at least two electrodes, (b) an ionic strength of an ionic buffer within the microfluidic device, and (c) electrostatic or hydrodynamic properties of the microfluidic device and electrostatic or hydrodynamic properties of the plurality of molecules or particles of interest, or to apply a voltage routine that applies a primary voltage to load at least a second portion of the plurality of molecules or particles of interest into the corresponding parking chambers and applies a secondary voltage that is greater than a 50% loading efficiency for a first size of molecule and is less than a 50% loading efficiency for a second size of molecule, thereby selectively loading the plurality of nanoslits with a portion of the plurality of molecules or particles of interest having a size distribution that is weighted more heavily toward the first size when compared with the plurality of molecules or particles of interest.

10. The system of claim 9, the system further comprising a heater or a cooler configured to heat or cool liquid within the microfluidic device.

11. The system of claim 9, the system further comprising a temperature measurement device configured to measure a temperature of fluid within the microfluidic device.

12. The system of claim 9, the system further comprising a spectrometer configured to optically interrogate molecules or particles of interest located in the microfluidic device.

13. The system of claim 12, wherein the spectrometer has sufficient spatial resolution to distinguish between molecules or particles of interest loaded in adjacent nanoslits.

14. The system of claim 12, wherein the spectrometer is configured to monitor an occupancy status of one or more of the plurality of parking chambers or one or more of the plurality of nanoslits.

15. The system of claim 12, wherein the spectrometer is a fluorescence microscope.

16. The system of claim 9, wherein the power supply controller is programmed with or configured to receive the electrostatic or hydrodynamic information of the plurality of molecules or particles of interest, the electrostatic or hydrodynamic information of the microfluidic device, buffer ionic strength information regarding the ionic buffer within the microfluidic device, or a combination thereof.

17. The system of claim 9, wherein the power supply routine is configured to apply the first voltage for the first time interval, the second voltage for the second time interval, and the third voltage for the third time interval, wherein the first voltage and the first time interval are configured to cause the at least a portion of the plurality of parking chambers to be occupied by one and only one molecule or particle of interest, wherein the second voltage and the second time interval are configured to cause the at least a portion of the plurality of nanoslits to be loaded with one and only one molecule or particle of interest from the at least a portion of the plurality of parking chambers, and wherein the third voltage and the third time interval are configured to allow the molecules or particles of interest loaded in the at least a portion of the plurality of nanoslits to assume the dumbbell configuration.

18. The system of claim 9, wherein the power supply routine is configured to selectively load the at least a portion of the plurality of parking chambers with one and only one of the plurality of molecules or particles of interest under conditions where motion of the selectively loaded molecules or particles of interest is at least partially aligned with the direction of electroosmotic forces, the power supply routine utilizing (a) the geometry of the microfluidic device relative to the at least two electrodes, (b) the ionic strength of the ionic buffer within the microfluidic device, and (c) the electrostatic or hydrodynamic properties of the microfluidic device and the electrostatic or hydrodynamic properties of the plurality of molecules or particles of interest.

19. The system of claim 9, wherein the power supply routine is configured to apply a voltage routine that applies a primary voltage to load at least a second portion of the plurality of molecules or particles of interest into the corresponding parking chambers and applies a secondary voltage that is greater than a 50% loading efficiency for a first size of molecule and is less than a 50% loading efficiency for a second size of molecule, thereby selectively loading the plurality of nanoslits with a portion of the plurality of molecules or particles of interest having a size distribution that is weighted more heavily toward the first size when compared with the plurality of molecules or particles of interest.

* * * * *

UNITED STATES PATENT AND TRADEMARK OFFICE
CERTIFICATE OF CORRECTION

| | |
|---|---|
| PATENT NO. | : 11,213,825 B2 |
| APPLICATION NO. | : 16/614003 |
| DATED | : January 4, 2022 |
| INVENTOR(S) | : David Charles Schwartz et al. |

It is certified that error appears in the above-identified patent and that said Letters Patent is hereby corrected as shown below:

In the Specification

Column 16, Line 2, "A" should be --$\lambda$--.

Column 17, Line 42, "02" should be --$O_2$--.

Signed and Sealed this
Seventh Day of February, 2023

Katherine Kelly Vidal
*Director of the United States Patent and Trademark Office*